US010918305B2

(12) United States Patent
Kuntz et al.

(10) Patent No.: US 10,918,305 B2
(45) Date of Patent: Feb. 16, 2021

(54) METHOD AND SYSTEM FOR 4D RADIOLOGICAL INTERVENTION GUIDANCE (4D-CATH)

(75) Inventors: Jan Kuntz, Romerberg (DE); Soenke Bartling, Heidelberg (DE); Marc Kachelriess, Nuremberg (DE)

(73) Assignees: Klinikum Mannheim Gmbh Universitätsklinikum Medizinische, Erlangen (DE); Fakultät Mannheim Der Universität Heidelberg, Erlangen (DE)

( * ) Notice: Subject to any disclaimer, the term of this patent is extended or adjusted under 35 U.S.C. 154(b) by 339 days.

(21) Appl. No.: 13/991,550

(22) PCT Filed: Dec. 16, 2011

(86) PCT No.: PCT/EP2011/073091
§ 371 (c)(1),
(2), (4) Date: Jul. 26, 2013

(87) PCT Pub. No.: WO2012/084726
PCT Pub. Date: Jun. 28, 2012

(65) Prior Publication Data
US 2013/0303884 A1 Nov. 14, 2013

Related U.S. Application Data

(60) Provisional application No. 61/425,308, filed on Dec. 21, 2010.

(51) Int. Cl.
*A61B 5/06* (2006.01)
*G06T 11/00* (2006.01)
(Continued)

(52) U.S. Cl.
CPC ............ *A61B 5/062* (2013.01); *A61B 1/2676* (2013.01); *A61B 5/0042* (2013.01);
(Continued)

(58) Field of Classification Search
None
See application file for complete search history.

(56) References Cited

U.S. PATENT DOCUMENTS

2005/0182295 A1* 8/2005 Soper .................. A61B 1/0008
600/117
2005/0251010 A1* 11/2005 Mistretta ................ A61B 6/025
600/407

(Continued)

OTHER PUBLICATIONS

Peters et al. "Active Guidewire Tracking with Real-Time Undersampled Projection Reconstruction." Proc. Intl. Soc. Mag. Reson. Med. 10 (2002).*
International Search Report for corresponding PCT/EP2011/073091 dated Jun. 28, 2012.
Kuntz, et al., "Towards 4D Intervention Guidance Using Compressed Sensing", Proceedings of the 11$^{th}$ International Meeting on Fully 3D Image Reconstruction in Radiology and Nuclear Medicine, Jul. 11, 2011, pp. 347-350.
(Continued)

*Primary Examiner* — Amelie R Davis
(74) *Attorney, Agent, or Firm* — Kilpatrick Townsend & Stockton LLP

(57) ABSTRACT

An imaging method for radiologically guiding an instrument during medical interventions on an object is disclosed. First, a prior volumetric image of the object is provided, followed by periodically providing a current volumetric image on-the-fly during the intervention to an operator by measuring an undersampled set of projections of the object and reconstructing the current image based on changes between the prior volumetric image or an updated prior image and the undersampled set of projections. The method and corresponding system are used for radiologically guiding medical interventions on an object. The system includes a first image provider, an imaging apparatus for measuring undersampled sets of projections, and a processor. The processor communicates with the imaging apparatus for providing updated images on-the-fly during the intervention by reconstructing the updated image based on changes between the first image or an update of the first image and the undersampled sets of projections.

22 Claims, 14 Drawing Sheets

(51) Int. Cl.
  *A61B 1/267* (2006.01)
  *A61B 5/00* (2006.01)
  *A61B 5/055* (2006.01)
  *A61B 6/03* (2006.01)
  *A61B 6/00* (2006.01)

(52) U.S. Cl.
  CPC ............ *A61B 5/0044* (2013.01); *A61B 5/055* (2013.01); *A61B 6/032* (2013.01); *A61B 6/501* (2013.01); *A61B 6/503* (2013.01); *G06T 11/006* (2013.01); *A61B 6/405* (2013.01); *A61B 6/542* (2013.01); *G06T 2211/412* (2013.01); *G06T 2211/428* (2013.01); *G06T 2211/436* (2013.01)

(56) References Cited

U.S. PATENT DOCUMENTS

| | | | |
|---|---|---|---|
| 2006/0193428 A1* | 8/2006 | Heismann | A61B 6/032 378/4 |
| 2007/0010731 A1 | 1/2007 | Mistretta | |
| 2008/0199063 A1* | 8/2008 | O'Halloran | G01R 33/4824 382/131 |
| 2010/0303196 A1* | 12/2010 | Zou | A61B 6/032 378/5 |
| 2010/0310144 A1 | 12/2010 | Chen et al. | |
| 2011/0058724 A1* | 3/2011 | Claus | G06T 11/006 382/132 |

OTHER PUBLICATIONS

Chen, et al., "Prior image constrained compressed sensing (PICCS): a method to accurately reconstruct dynamic CT images from highly undersampled projection data sets", Medical Physics, vol. 35, No. 2, Feb. 1, 2008, pp. 660-663.

Schirra, et al., "Toward True 3D Visualization of Active Catheters Using Compressed Sensing", Magnetic Resonance in Medicine, 2009, pp. 341-347.

Sidky, et al., "Image reconstruction in circular cone-beam computed tomography by constrained, total-variation minimization", Phys. Med. Biol., 53, 2008, pp. 4777-4807.

Bain, et al., "Evaluation of sparse-view reconstruction from flat-panel-detector cone-beam CT", Phys. Med. Biol., 55, 2010, pp. 6575-6599.

Chen, et al., "Time-Resolved Interventional Cardiac C-arm Cone-Beam CT: An Application of the PICCS Algorithm", IEEE Transactions on Medical Imaging, vol. 31, No. 4, Apr. 2012, pp. 907-923.

Langet, et al., "Medical Imaging Computing and Computer-Assisted Intervention", MICCAI 2011, pp. 97-104.

Qi, et al., "Performance studies of four-dimensional cone beam computed tomography", Phys. Med. Biol., 56, 2011, pp. 6709-6721.

Gupta, et al., "Flat-Panel Volume CT: Fundamental Principals, Technology, and Applications", Radio graphics, 2008, 15 pages.

Feldkamp, et al., "Practical cone-beam algorithm", J. Opt. Soc. Am. A, vol. 1, No. 6, Jun. 1984, pp. 612-618.

* cited by examiner

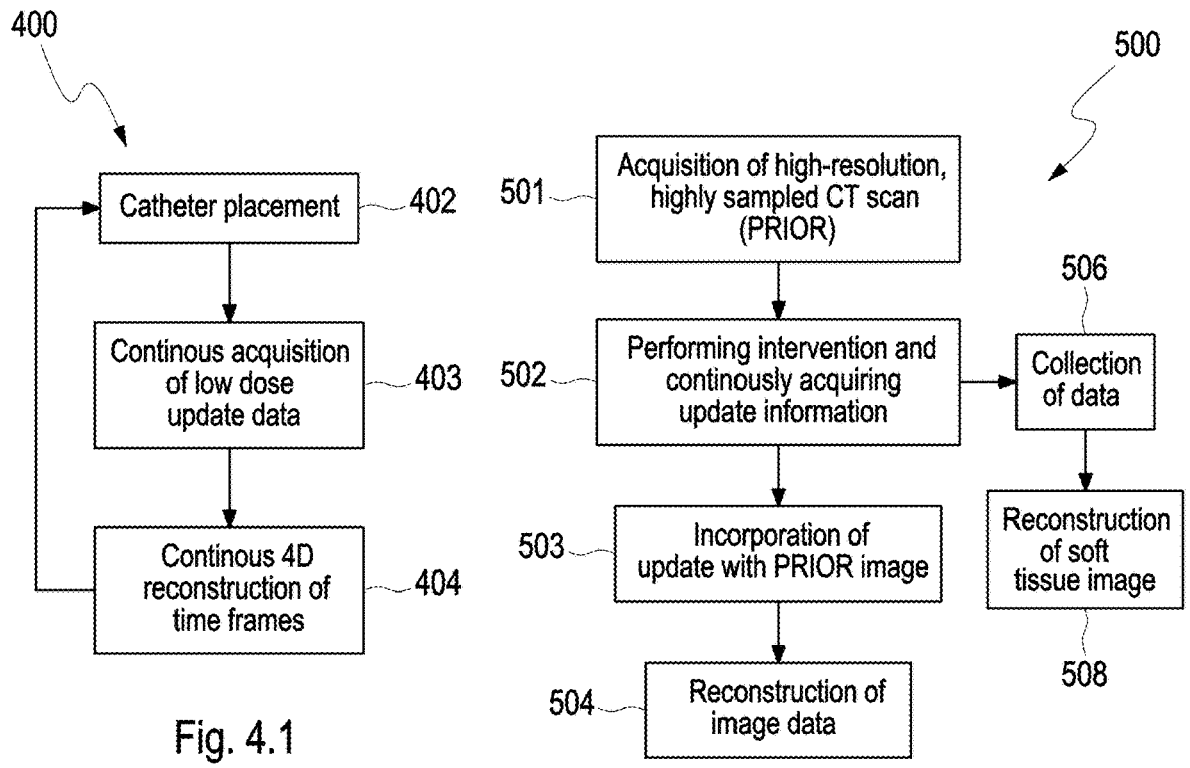
Fig. 4.1
Fig. 4.2
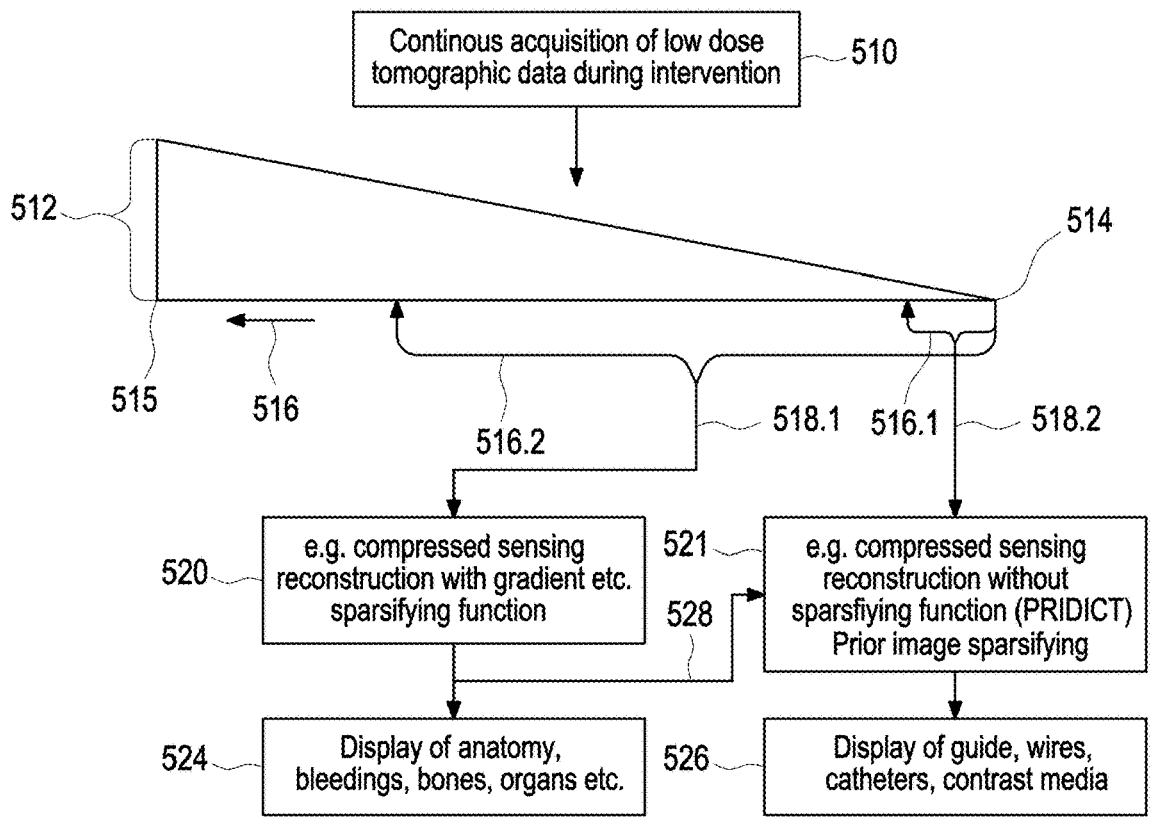
Fig. 5

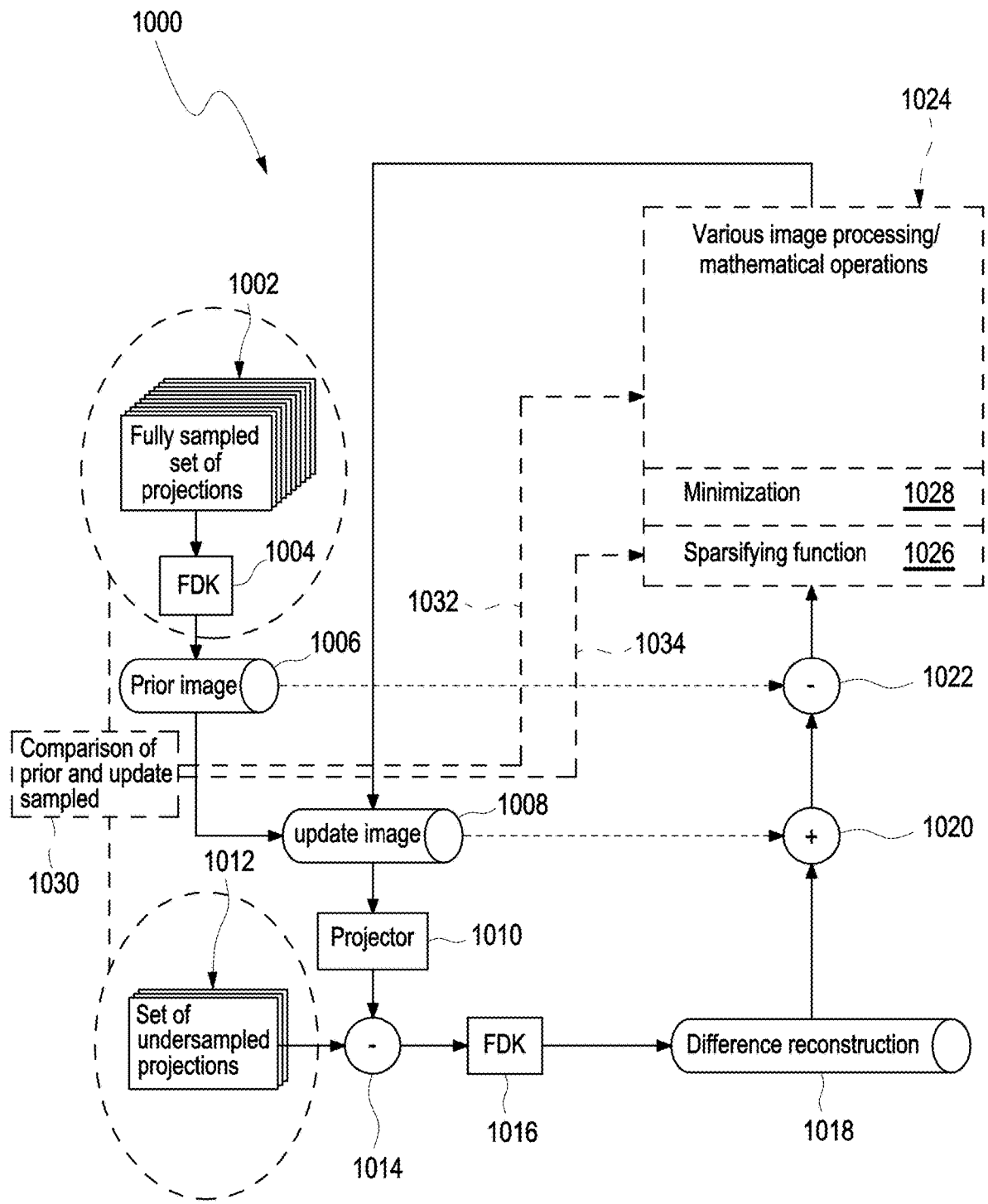
Fig. 10.1

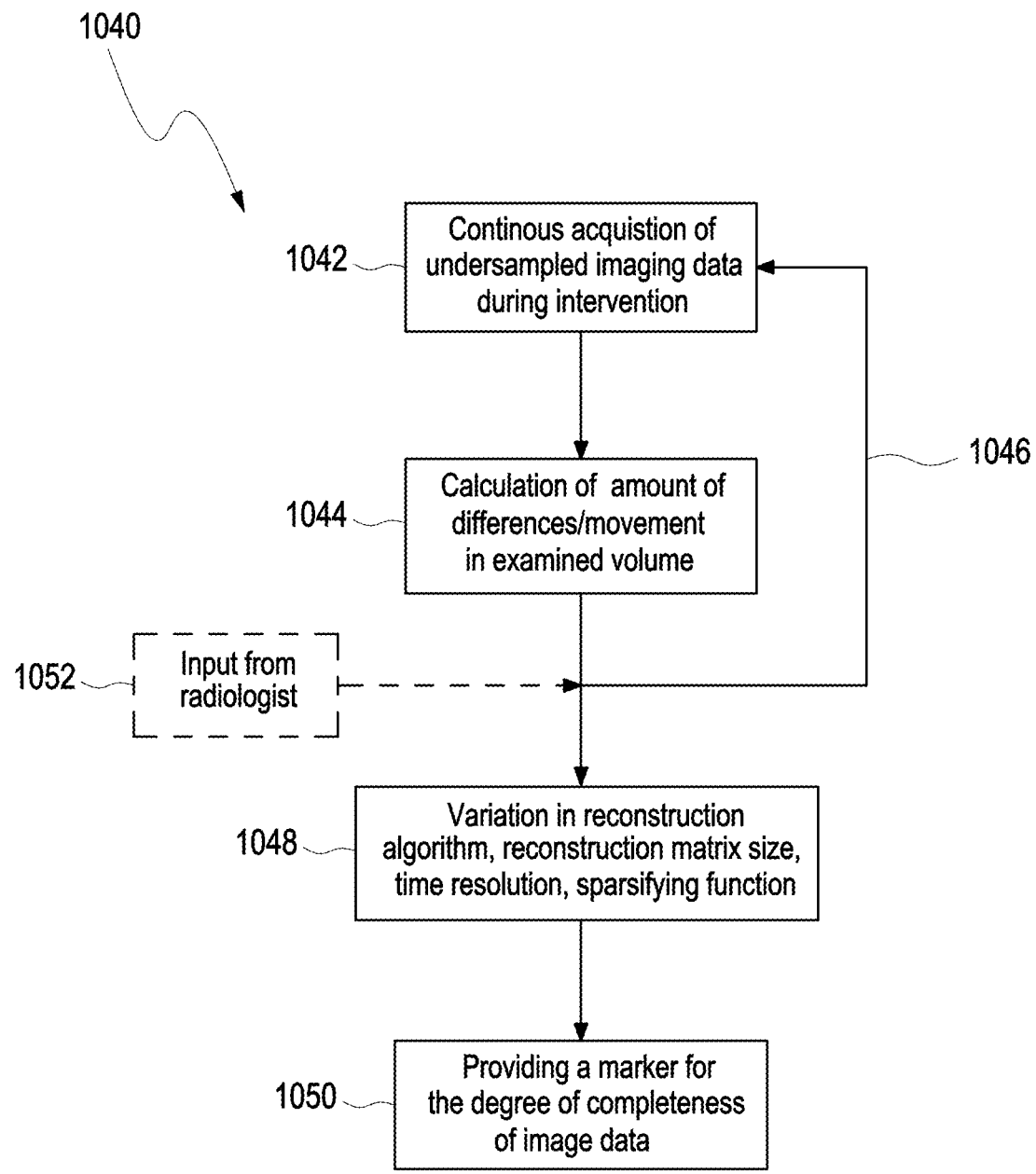
Fig. 10.2

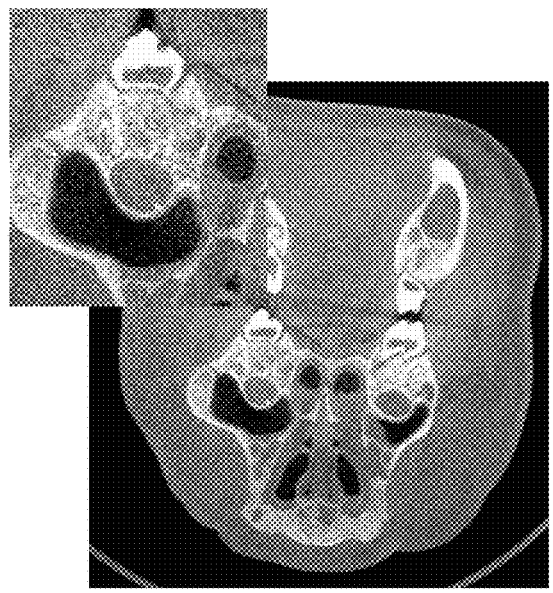
Fig. 12.1
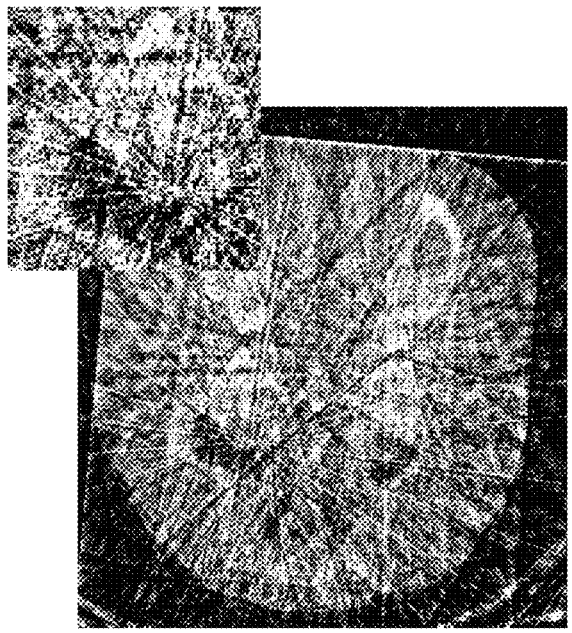
Fig. 12.2
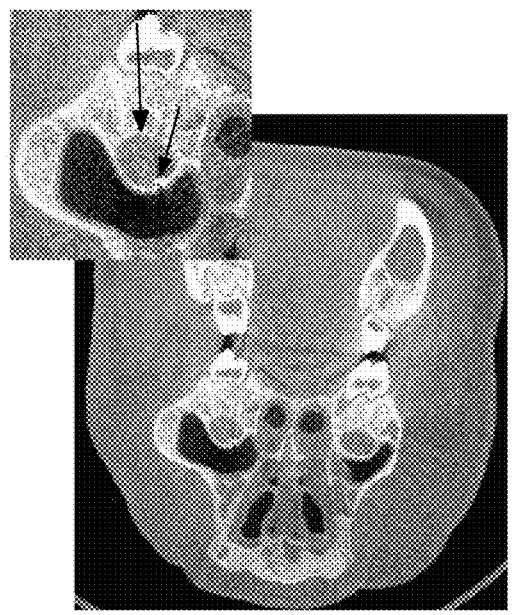
Fig. 12.3

METHOD AND SYSTEM FOR 4D RADIOLOGICAL INTERVENTION GUIDANCE (4D-CATH)

This application is a national stage application of PCT/EP2011/073091 filed Dec. 16, 2011, which claims priority to U.S. Provisional Application No. 61/425,308, filed Dec. 21, 2010, the entire contents and disclosures of which are hereby incorporated by reference.

FIELD OF INVENTION

The present invention relates to an imaging method for radiologically guiding an instrument during medical interventions on an object. The invention further refers to a system for radiologically guiding medical interventions on an object.

Radiologically guided interventions are currently limited by known imaging methods, because known imaging methods do not allow 4D imaging (3 spatial dimensions plus time), while radiological interventions are a 4D process. Current means of intervention guidance are either continuous projective imaging (X-ray fluoroscopy) or manipulate-and-shoot computed tomography (CT) imaging. Both methods leave the interventionist with a high degree of uncertainty regarding the position of his instruments and the current surroundings.

Recently, there have been approaches for using magnetic resonance (MR) to guide interventions. C. O. Shirra et al. (Magnetic Resonance in Medicine 62:341-347, 2009) describe a framework for visualization of active catheters in 3D. In this framework compressing sensing is employed to gain high undersampling factors. Here constraints are introduced taking into account prior knowledge of catheter tube geometry and catheter motion over time to improve and accelerate image reconstruction. Furthermore, given the incremental motion of the catheter, the known position of the device of the preceding timeframe is used to penalize the reconstruction problem. In particular, the method of Schirra et al. includes the acquisition of data with randomly undersampled phase encodes; image reconstruction through constrained compressed sensing reconstruction and curve fitting the catheter outline, which can be displayed on a high resolution roadmap. Nevertheless, MR imaging still requires special arrangements to detect and visualize the instruments used for interventions. In this respect CT is due to the nature of X-Rays easier to handle, but present CT techniques such as CT-fluoroscopy require excessive radiation doses, preventing them from being routinely used.

For the reconstruction of X-ray CT images different reconstruction frameworks with sparsely sampled view angles have been proposed in order to reduce the radiation dose for the patient. In G.-H. Chen et al. (Medical Physics 35 (2), February 2008) the PICCS algorithm is presented, which reconstructs target image sequences of one measured dataset and a prior image reconstructed from the same dataset. In the reconstructed prior image the dynamic information is lost, but static structure in the image are well reconstructed. The prior image is therefore used to subtract the static structure from the target image for each time frame. A further sparsifying transform (discrete gradient) is used to further sparsify the difference. For the reconstruction of dynamic data, the data set is further gated using the simultaneously recorded electrocardiogram.

E. Y. Sidky et al. (Physics in Medicine and Biology 53, 4777, 2008) and J. Bain et al. (Physics in Medicine and Biology 55, 6575, 2010), disclose reconstruction algorithms based on constraint total-variation (TV) minimization to reconstruct data with sparsely sampled view angles. Here, the optimization selects the image with the minimum TV amongst those that satisfy a given constraint.

In G.-H. Chen et al. (IEEE Transaction on Medical Imaging PP, 1-1, October 2011), a data acquisition scheme and an imaging reconstruction method for time-resolved cardiac imaging particularly relevant to image guidance for accurate procedural planning and cardiac functional evaluations is described. The data acquired during a single gantry rotation of a C-arm system is reconstructed to a prior image using the classical FDK algorithm (filtered back projection algorithm according to Feldkamp, Davis and Kress). Then the data is gated into the different cardiac phases resulting in undersampled sets for each phase, that are reconstructed through the prior image constraint compressed sensing (PICCS) algorithm utilizing the reconstructed prior image.

H. Langet et al. (MICCIA 2011, Part I, LNCS 6891, p 97-104, 2011) discloses a method for 3D reconstruction of rotational angiography based on an iterative filtered back-projection approach that includes a sparsity constraint called soft background subtraction. This approach is particularly useful when injecting a contrast medium particularly leading to late vessel opacification. Z. Qi et al. (Physics in Medicine 56, 6709, 2011) discloses a 4D cone beam CT method which enables the detection of e.g. respiratory motion. The acquired data is binned into the different respiratory phases and reconstructed using PICCS. From the reconstructed 4D cone beam computes tomography images, the motion trajectory for an object is extracted using deformable registration methods.

However, there is still a need for real time CT imaging for guiding interventions, which reduces the exposure of the patient to ionizing radiation to a minimum.

OBJECT OF THE INVENTION

The present invention aims to provide a method for true 4D imaging which overcomes above mentioned limitations to improve radiological guided interventions. It is a further object of the present invention to provide a method for fully CT guided medical intervention providing three-dimensional information in real time during the intervention. The present invention particularly aims at providing 4D CT imaging that avoids excessive radiation dose for the patient and can be routinely used in medical applications.

According to the invention, an imaging method for radiologically guiding an instrument during medical interventions on an object is proposed, which comprises the following steps:
a) providing a first image of said object followed by
b) providing updated images on-the-fly during the intervention to an operator by measuring an undersampled set of projections of said object and reconstructing said updated image based on changes between said first image or an update of said first image and said undersampled set of projections.

Additionally, according to the invention, a system for radiologically guiding medical interventions on an object, according to the method previously explained, is proposed. Such a system comprises:
means to provide a first image of the object;
an imaging apparatus measuring undersampled sets of projections;
processing means in communication with the imaging apparatus for providing updated images on-the-fly during the intervention by reconstructing said updated image based on changes between said first image or an update of said first image and said undersampled set of projections.

The proposed imaging method and imaging system for radiologically guiding the instrument during medical interventions allow for dynamic real-time imaging during the course of the intervention. Thus, volumetric data is acquired in close, timely consecution allowing the operator to control and monitor the course of the intervention and particularly the movement of the instrument in three spatial dimensions. The proposed method and system for medical imaging aim to provide the temporal changes in the object to be imaged, such as instrument movements, by measuring a small number of projections for the undersampled sets of projections. This way, the radiation dose, the patient is exposed to, can be reduced to a minimum, while still providing sufficient information on temporal changes, such as instrument movement.

Furthermore, the proposed imaging method and imaging system allow an operator to monitor and hence to control the intervention. Such interventions can be performed on body parts, such as the cardiovascular system, tubular organ structures or on the brain, which exhibit complicated three-dimensional structures. In particular, the time component, i.e. the dynamics of the intervention, play an important role in order to ensure safe performance. This provides the interventionist with a high degree of certainty in the way the intervention is performed and thus, reduces the risk for the patient during intervention.

Thus, the proposed method facilitates fully guided interventions based on imaging, which is particularly relevant to interventions such as catheter interventions, bronchoscopy interventions, implantation of cardiac pacemakers or positioning of stents. Hence, maneuvering in complicated three-dimensional structures becomes easier and misplacement of e.g. stents or injury due to e.g. rupture of vessels can be avoided. Overall, the imaging method according to the present invention provides full control in three-spatial dimensions including temporal changes during the course of the intervention.

In contrast to known systems, where the projections that are used for guidance cannot be used for tomographic reconstruction, the invention allows to use the projection data for the reconstruction of several pieces of information relying on the same data acquisition. This significantly reduces the relative radiation costs. Additionally, through the application of tomographic imaging a lower concentration of contrast media is detectable.

Furthermore, the invention allows novel intervention concepts to become feasible. For instance, biopsies can be combined with endoscopic or intravascular accesses. The intravascular access route can be used for biopsies of extravascular structures, e.g. pancreas biopsies through the superior mesenteric artery. Extrabronchial masses can be accessed through a bronchius, while the needle towards the mass is then imaged using the said tomographic imaging. In particular at present, no tomgraphic imaging is available, which is why the biopsie of extraluminal lesions using endoscopes is limited to the optically, visible wall lesions.

In the sense of the present invention, imaging refers to tomographic imaging providing a volumetric image of an object as reconstructed from one-dimensional or two-dimensional projections. A projection hereby represents a two-dimensional (once integrated) or a one-dimensional (twice integrated) image of a three-dimensional distribution at specific projection solid angles of the source-detector assembly with respect to the object to be imaged.

In particular, medical imaging is a technique and process to create images of the human body for clinical purposes. The object to be imaged can either comprise the full body of a patient or parts and functions thereof. Typical imaging techniques used in this area are tomographic imaging techniques, such as magnetic resonance imaging (MM) or computer tomography (CT). In the case of MM non-ionizing radio frequency (RF) signals are used to acquire images. CT, on the other hand, uses X-rays (a type of ionizing radiation) in order to image objects. Owing to the dose X-rays carry, only a restricted number of exposures can be performed and the number of projections to be measured is to be kept at a minimum. However, instrument detection via X-rays is due to the nature of radiation simpler than instrument detection through MR-signals. In a preferred embodiment of the invention, said imaging method can be based on ionizing radiation particularly X-rays, wherein the undersampled set of projections is measured with a minimized radiation dose.

The method according to the present invention provides updated images "on-the-fly", meaning measurements, calculations and modifications take place without significant time delay during the intervention. Hence, the method provides a way of real-time imaging during medical interventions. Furthermore, the real time images are provided to an operator, who can be the interventionist or a medical robot, to further support the course of the intervention. Lastly, an updated image represents an image that includes the latest temporal changes recorded during the intervention.

In the sense of the present invention, an "undersampled set of projections" represents a sparsely sampled set of projections, meaning the number of measured projections violate the Shannon-Nyquist sampling theorem. In view of the present invention, the Shannon-Nyquist theorem is in the image domain given by the highest represented frequency f. The sampling rate must be larger than 2f to fulfil the Shannon-Nyquist theorem. A pixel corresponds to a data point in a matrix representing the image. In contrast to an undersampled set a fully sampled set fulfils the Shannon-Nyquist sampling theorem and includes an appropriate number of projections essentially uniformly distributed between 0° and (180°+cone angle). Here essentially uniformly encompasses deviations of up to 10%. In practical interventional radiology, the undersampling factor can lie in the order of 10-30 resulting in 8-35 frames per reconstruction.

In one aspect of the present invention, said first image, said update of said first image and said updated images comprise volumetric images of the object to be imaged. Here, the first image, which includes the static structure of the object may be reconstructed from at least one undersampled set of projections, at least one fully sampled set of projections or a combination hereof. Particularly, said first image can comprise a high-resolution volumetric image of the object, which can be acquired prior to the intervention. Such a high resolution volumetric image can be produced by measuring a fully sampled set of projections using CT imaging or any other medical imaging modalities. Another option comprises to provide a high resolution volumetric image from a database, where for example previously recorded images of the object to be imaged are stored. This way a reconstruction for Prior Image Dynamic Computed Tomography (PRIDICT) can be realized allowing for real-time interventional guidance.

In a further aspect of the invention, a first image reconstructed from an undersampled set of projections can be improved during the course of the invention by incorporating any projections measured to reconstruct the updated image into the first image leading to an updated first image.

The update of the first image thus encompasses the first image and at least parts of one or more updated images reconstructed in previous runs during the intervention. Previous runs in this context comprise any reconstructed image or equivalently any projections that have been acquired at some time before the current updated image. Thus, the iterative method provides updated images in real-time, where a reconstruction performed at a point $T_2$ in time may include an update of the first image, which again, comprises any updated images computed at earlier points in time $T_1 < T_2$.

In another aspect of the present invention, the update of the first image is a sliding prior defragmenting updated images of previous runs. Thus, the update of the first image at a point $T_2$ can incorporate updated images produced at any point $T_1 < T_2$, wherein the update of the first image is successively updated for every reconstruction performed. In this embodiment, the projections of the update scans are preferably acquired at projection angels that are different from earlier projection angles such that after several rotations a new-fully sampled dataset is produced, which can be used as update of the first image. This is particularly advantageous when movement of the object occurs during the intervention. Such movement may e.g. include displacement of the patient relatively to the imaging system.

In another embodiment of the present invention, not only changes, which progress fast in time, such as catheter movement, but also slower changes, such as bleedings, may be visualized by storing the undersampled sets of projections measured on-the-fly during the intervention for a delayed reconstruction of soft tissue contrast.

In another aspect of the invention, the method for reconstructing the updated image based on changes between the first image or the update of the first image and the undersampled set of projections is proposed, which utilizes a compressed sensing framework. This framework is generally known for application in CT (see e.g. E. Y. Sidky et al., Imaging Reconstruction in Circular Cone-Beam Computer Tomography for Constrained, Total-Variation Minimization, Phys. Med. Biol., 2008, 53, 4777-4807). In general, compressed sensing allows for image reconstruction from randomly undersampled data violating the Shannon-Nyquist sampling theorem. A necessary condition for a successful reconstruction thereby is the sparsity of the given data in any transform domain, such as the image domain. For the highest represented frequency f in the image domain and the sampling rate corresponding to the number of measured projections D, image recovery is possible as long as $D < 2f$. Assuming the projections are measured at random projection angles, the image can be recovered from D measurements with high probability by solving the L1 optimization problem, wherein L1 denotes the norm defined by the sum of the absolute values in each pixel.

In one realization the reconstruction algorithm according to the present invention is an iterative reconstruction algorithm. In a one step of this algorithm the amount of changes between different images taken at different points in time during the intervention can be determined by forward projecting the first image or the update of the first image according to the projections comprised in the undersampled set of projections. Thus, a set of equivalent projections based on the first image or on the updated of the first image can be provided in order to perform a subtraction operation between equivalent projections of the undersampled set of projections and the projections resulting from the first image or its update. Here, equivalent projections refer to forward projected images having the same projection angles.

From the difference projections, a difference volumetric image may be reconstructed. Through the subtraction operation, static parts of the object to be imaged, which are included in the first image or the updated first image, are effectively subtracted from the measurement characterizing the updated image. Therefore, the updated image basically represents the temporal change in the object to be imaged. During, for instance catheter interventions, this temporal change is given by the movement of the instrument.

In another implementation of the invention, the reconstruction includes an iterative minimization of a number of significant pixels, optionally including further sparsifying functions, which might be applied after reconstruction of the differences. The number of significant pixels thereby includes all pixels signifying the temporal changes, and thus, representing the dynamic rather than the static structure of the image. Further sparsifying functions may include gradient operations, wavelet transformations, curvelet transformations, contourlet transformations or a combination thereof. Such transformations aid to reduce the number of significant pixels by further sparsifying the image to be reconstructed.

In a further implementation of the reconstruction algorithm, the algorithm itself or the scan parameters can be influenced by the amount of changes between successive measurements of projections. A combination of different sparsifying transforms and/or one tunable sparsifying transforms can be used in different configurations during one reconstruction to correctly reconstruct different structures, e.g. point-like or curve-like structures. Alternatively or additionally, the weight of different sparsifying transforms can be varied e.g. according to the sparseness of the transformed image. In particular, the influence by the amount of change on the algorithm can include a further sparsification of the image, if the changes are less significant with time.

Alternatively, the sparsification may solely be based on the difference excluding further sparsification, if there are significant changes in time. Significant temporal changes are, for example instrument movements, in contrast to less significant temporal changes, which may be related to vessel bleedings or the like. Here, significant changes can signified by the rate of change, which may be faster than one changing feature corresponding to one or more changing pixels in the image per minute, preferably per 30 seconds. In contrast, a less significant change may constitute less than one changing feature corresponding to one or more changing pixels in the image per minute, preferably per 1.5, particularly preferably per 2 minutes. Furthermore, the scan parameters such as the number of projections in the undersampled set of projections and/or the dose rate per projection can be adapted according to the amount of changes between measurements and/or according to an input provided by the operator.

In a further implementation of the present invention, the at least one further sparsifying function included in the reconstruction depends on the amount of data that has been acquired before the actual present. In this context, the actual present signifies a range in time, wherein the longer ago from the present the higher the amount of low-dose tomographic data that has been acquired during the intervention. Thus at a point, where the amount of data for tomographic reconstruction only comprises a few projections, the amount of data is small and updated images can be reconstructed excluding sparsifying functions, preferably by minimization directly in the image domain through PRIDICT (Prior Image Dynamic Computed Tomography). If the amount of data for tomographic reconstruction comprises more projections, for example data stored from previous runs, images can be reconstructed with sparsifying function. In particular, updated images can be reconstructed with no further sparsifying function. Additionally or alternatively, the reconstruction of data stored from previous runs can include at least one sparsifying function.

The prior data and update information can be acquired over a limited angle orbit around the patient. The reconstruction algorithm can use information that it derives by comparing the update scan with the prior scan to correct for limited angle CT reconstruction artifacts or distortions. This can be done by calculating a local distortion parameter by comparing the sparsely sampled limited angle updates with the well sampled prior scan.

In one embodiment the differences of projections of several rotations are compared. In case of little differences the projection acquisition rate or radiation dose is reduced. This can also be used to compensate patient movements that would yield great differences in the acquired projection data and hence require more radiation dose to compensate for it. In one embodiment the radiologist can influence the effects that the amount of differences has on the reconstruction algorithm or data acquisition (FIG. 9). E.g. by selecting certain programs or modes of the system and by pressing a handle or a pedal the radiation dose will be much more increased with the same amount of changes in the examined volume.

In yet a further implementation of the algorithm, the reconstruction of the updated image includes motion compensation. Motion compensation describes a method, which tracks motion in successive images and formulates the motion in terms of a transformation of one image to a successive image or vice versa. Such motion compensation is usually based on comparing corresponding features in successive images and identifying motion vectors, which may be used to build up a motion vector field. In particular, through motion compensation periodic and/or non-periodic motion of the object or a structure within the object to be imaged can be compensated for in the reconstruction of the updated images. Specifically, periodic motion compensation can be performed through gating measured projections into different phases of the periodic motion and utilizing the gated projections for reconstruction. For gating the cycle of the periodic motion is typically fragmented in to several intervals signifying the phases of motion and the projections are distributed into the corresponding intervals during measurement. In interventions periodic motions can result from the respiratory and/or the cardiac motion. During the course of the intervention, respiratory and/or cardiac motion are recorded providing a type of reference signal for the gating. Measured projections are then distributed into the different phases according to that reference signal.

In another implementation periodic motion compensation can be performed through a transformation mapping of images into one phase of the periodic motion. This can be realized by applying deformations via motion-vector fields. Examples for such algorithms are the McKinnon-Bates algorithm or the Phase-Correlated Feldkamp algorithm. In comparison to gating, transformation mapping enables to use all the measured data for reconstruction, which further minimizes the radiation dose during intervention and still provides high image quality at all time points of a motion cycle. In another implementation the motion compensation will be performed by recording a fully sampled 4D dataset of the imaged object, e.g. the heart or the lung. From this data set motion vectors are calculated that can then be used to support the motion compensated reconstruction.

The updated images reconstructed iteratively during the course of the intervention can be displayed in real-time on a screen allowing for different representation modes which are chosen automatically or by the operator. The image diagnostically relevant for the physician is the sum of the first image including static structures and the temporal update giving the updated image. Therefore, the updated imaging including static and dynamic structure can be provided to the operator, preferably through a screen. The representation of such images may for instance be preset including either a full 3D representation of the object to be imaged and further parameters, which might be of interest during intervention guidance. Here, the 3D representation may comprise some solid or boundary model of the object to be imaged and in particular the relevant structures or functions therein. The representation mode can be selected from volume rendering, multiplanar reformations and all other means of medical image presentation. In a further version, image analyze tools are used to trace the intervention instruments in the data set and provide the interventionist with region of interest representations using e.g. curved multiplanar reformation, segmentation or similar tools.

Furthermore, with the updated image the operator can be provided with an indicator of the accuracy of the displayed image. This indicator of accuracy can depend, for instance, on the reconstruction parameters, such as matrix size or time resolution, the scan parameters, such as number of projections in the undersampled set, or the like. One indicator can be the total variation or other mean values of the displayed image to assess the difference between actual projections and forward projections through later reconstructed volumes.

According to the invention a computer program for performing above described method is proposed, when executing the computer program on a computer, particularly a high performance computing device (HPC). The computer program is preferably stored on a machine readable storage medium or on a removable CD-Rom, Flash memory, DVD or USB-stick. Additionally or alternatively, the computer program is provided on a server to be downloaded via, for example, a data network, such as the internet or another transfer system, such as a phone line or any wireless connection.

Further according to the invention, above described method is used during interventions on the cardiovascular system, during catheter intervention and/or for use in the implementation of cardiac pace makers. Further according to the invention, above described method is used during interventions on tubular organ structures, preferably lungs or kidneys, in positioning of stents in vessels or bronchi or used during bronchoscopy interventions. Further uses comprise interventions on the brain or angiography.

Additionally according to the invention, a system for radiologically guiding medical interventions on an object, according to above described method, is proposed. Such a system comprises:
  means for providing a first image of the object;
  an imaging apparatus measuring undersampled sets of projections;
  processing means in communication with the imaging apparatus for providing updated images on-the-fly during the intervention by reconstructing an updated image based on changes between said first image or an update of said first image and said undersampled set of projections.

Preferably, the system encompasses the necessary elements for providing the updated image to an operator, such as screens. Preferably, the system comprises the components described in the context of the method according to the invention in order to be capable of performing the same. A system of this type is particularly advantageous, since it allows monitoring and controlling movements of an instrument during medical interventions on an object in real-time.

In a preferred embodiment of the imaging system, the imaging apparatus is a tomographic system, such as a magnetic resonance imaging (MM) scanner or a computed tomography (CT) scanner, wherein the CT scanner comprises at least one X-ray source and at least one detector. Furthermore, the X-ray sources may differ in terms of the X-ray spectra and the detectors can provide means of energy differentiation. This way potential material differentiation is being used to influence the reconstruction algorithm and/or the dual-energy information is being used to extract further information on changes related to instrument movements.

In a further embodiment of the imaging apparatus, imaging parameters of the apparatus depend on the changes between said first image or an update of said first image and said undersampled set of projections. The imaging parameters of the imaging apparatus can influenced automatically or by an operator. For the operator to monitor and control the intervention, the system can include means to provide an input and/or an output to an operator. Preferably, the output comprises at least one updated image, at least one image produced by delayed reconstruction of soft tissue contrast and/or an indicator for an accuracy of displayed images.

BRIEF DESCRIPTION OF THE DRAWINGS

The subject-matter of the invention will be explained in more detail in the following with reference to preferred exemplary embodiments, which are illustrated in the attached drawings. The drawings show FIG. 1 an exemplary configuration of the 4D-CATH lab is shown (here 4D-CATH stands for 4D Catheter Advancement with Tomographic Help), FIG. 2 an illustration of a C-arm CT imaging device, FIG. 3 an illustration of the general CT acquisition process, FIG. 4.1 a flowchart of the general CT workflow for 4D-CATH, FIG. 4.2 a workflow of CT image acquisition and reconstruction, FIG. 5 an illustration of a time-dependent data acquisition, FIG. 6 an illustration of a sliding prior, FIG. 7 a flowchart showing the general structure of the PRIDICT reconstruction algorithm that can be used in 4D-CATH, FIG. 8 one embodiment of the PRIDICT reconstruction algorithm as shown in FIG. 7, FIG. 9 a further embodiment of the PRIDICT reconstruction algorithm as shown in FIG. 7, FIG. 10.1 yet a further embodiment of the PRIDICT reconstruction algorithm as shown in FIG. 7 including a method to influence the sparsifying function, FIG. 10.2 a flowchart of the CT image acquisition and reconstruction including influencing scan and/or reconstruction parameters, FIG. 11 yet a further embodiment of the PRIDICT reconstruction algorithm including a further method to influence the reconstruction algorithm, FIG. 12.1-.3 exemplary reconstruction of the guide wire moved in a pig's head, FIG. 13 an illustration of the PRIDICT reconstruction algorithm including motion compensation, FIG. 14 a flowchart for 4D intervention guidance and 3D road-mapping.

EMBODIMENTS ACCORDING TO THE INVENTION

Figure 1:
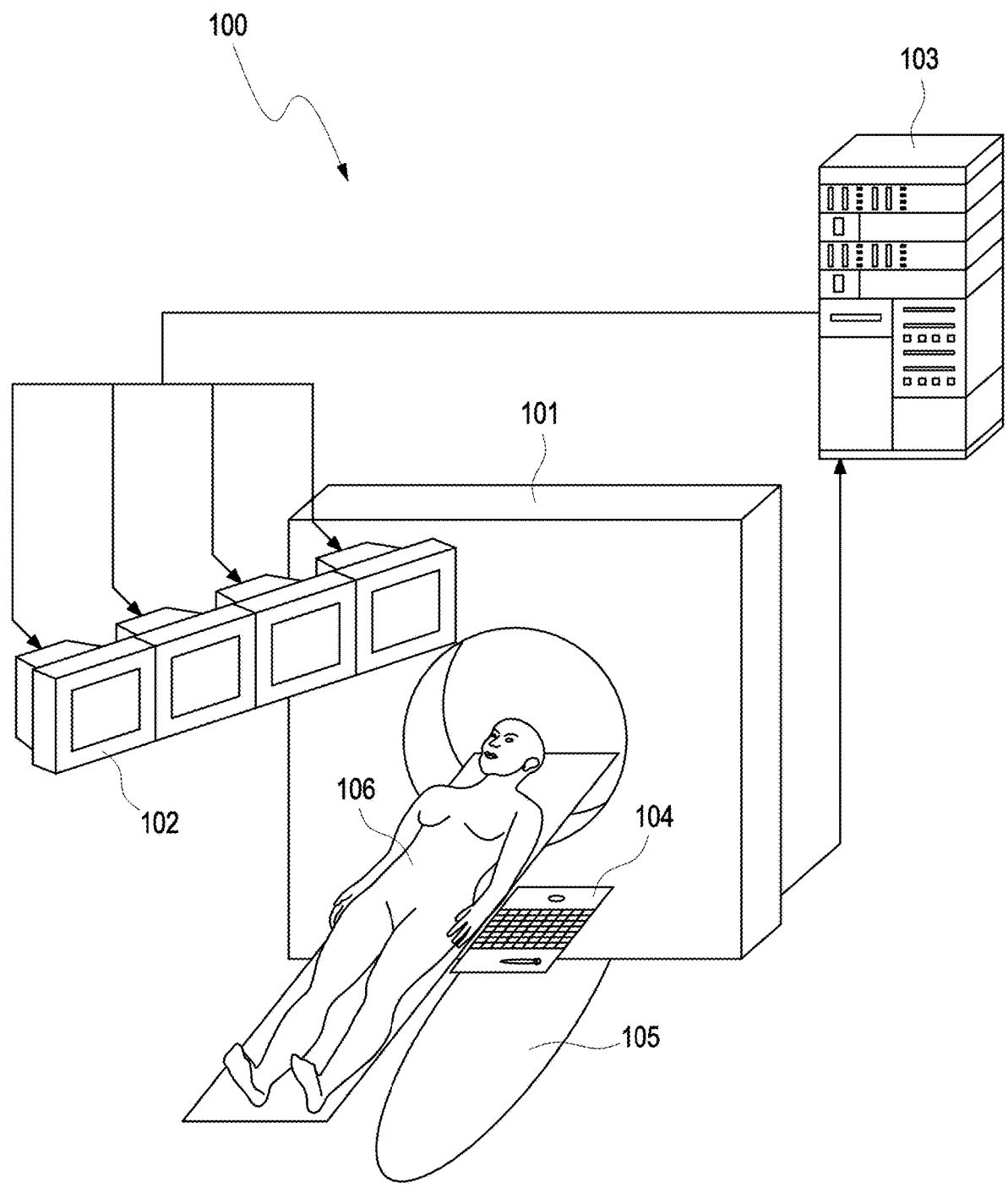

FIG. 1 shows an exemplary configuration of the 4D-CATH lab including a CT scanner 101 in communication with a high performance computing device (HPC) 103 further in communication with one display or an array of displays 102 to provide the operator 105 with imaging information for guiding the intervention. The tomography system 101 is directly connected to the HPC 103 like conventional clusters, GPU-systems, GPU-clusters, cloud systems or other mainframes, where the actual reconstruction of images is performed. Thus, the HCP 103 receives projections measured by the CT scanner 101 and sends reconstructed, updated images to at least one of the displays of the array of displays 102.

In an exemplary embodiment, the CT scanner 101 comprises a continuously rotating, gantry-based CT scanner 101 with a flat-panel detector. Such a system is for instance described in R. Gupta et al. (Flat-panel volume CT: fundamental principles, technology, and applications. Radiographics. 2008; 28(7):2009-2022). Other embodiments such as the CT scanner 101 shown in FIG. 2 can use an alternating direction scanning C-arm or O-arm scanner geometry. Compared to a gantry-based configuration such scanner geometries provide a space-saving solution, but the rotation time is limited.

During the course of the intervention the CT scanner 101 runs in a continuously tomographic acquisition mode, while the image acquisition can be pulsed. Here, the first rotation can be used to run a fully sampled acquisition mode and all following rotations are performed in undersampled acquisition mode. Prior to the intervention, the prior image can for instance be sampled using a gantry-based system with a frame-rate of 30 frames per second, a rotation time of 10s and a tube-current of 50 mA and tube voltage of 100 kV. During the course of the intervention, the temporal updates corresponding to undersampled sets of projections can be sampled with e.g. 18 frames per rotation, a tube current of 30 mA and a tube voltage of 100 kV. However, the scanning parameters may be adjusted according to the respective application.

During intervention the patient 106 is placed within the scanner system 101 and the information is provided to an operator, e.g. the interventionist 105, through the array of displays 102. Thereby the interventionist 105 stands next to the patient 106 and controls the intervention via the operator console 104. In other embodiments, the interventionist 105 can also be situated in a remote location. The operator console 104 further allows modifying all functions of the interventional CT system 101 and most parameters affecting the imaging, e.g. the reconstruction algorithm, are controlled by the interventionist 105.

During the intervention, a CT scanner system 101 acquires images of the patient 105. Typically, such systems comprise a source 201, 304 releasing electromagnetic radiation, preferably X-rays, and a detector 202, 306 detecting the released X-rays after having traversed the objection to the image 106, 302, 310, 203. Thus, a typical result of such a measurement comprises projections of a three-dimensional (3D) energy distribution. In this sense, a projection is a two-dimensional (once integrated) or 1-dimensional (twice integrated) distribution of the underlying 3D energy distribution at specific projections solid angles of the detector with respect to the object to be imaged. Therefore, in order to reconstruct a 3D image of the object to be imaged 106, 203, 302, 310 multiple projections are measured at different projection angles. From the multiple of projections a 3D image of the object to be imaged 106, 203, 310, 302 can be reconstructed.

Figure 2:
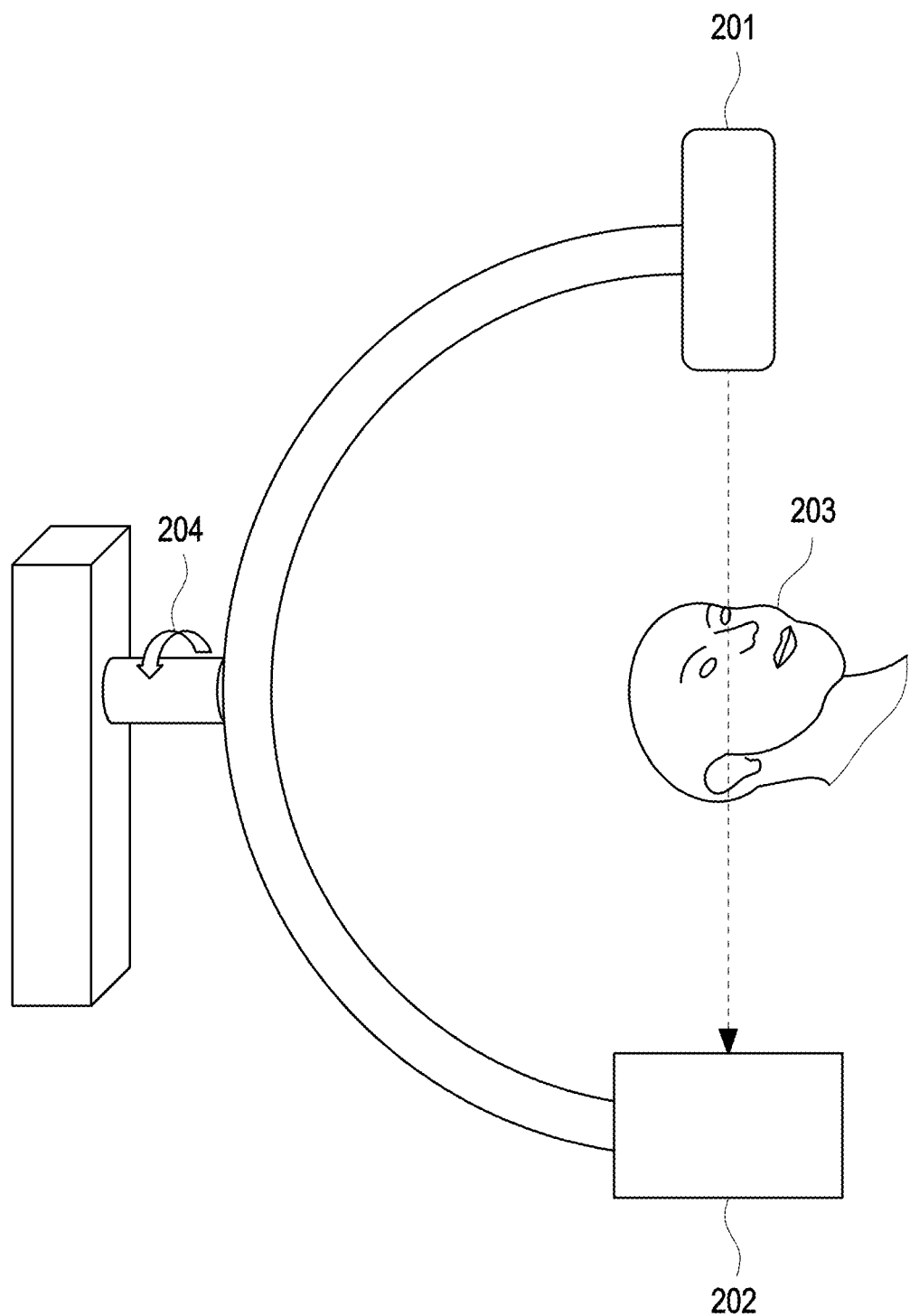

For measuring a multiple of projections, the CT scanner 101 typically comprises a gantry or C-arm-based construction for rotating the source 201, 304 and the detector 202, 306 around the object to be imaged 106, 203, 302, 310. FIG. 2 for example shows a C-arm-based CT imaging device with the source 201 and the detector 202 rotating around the object to be imaged, in this case the patient's head 203.

Figure 3:
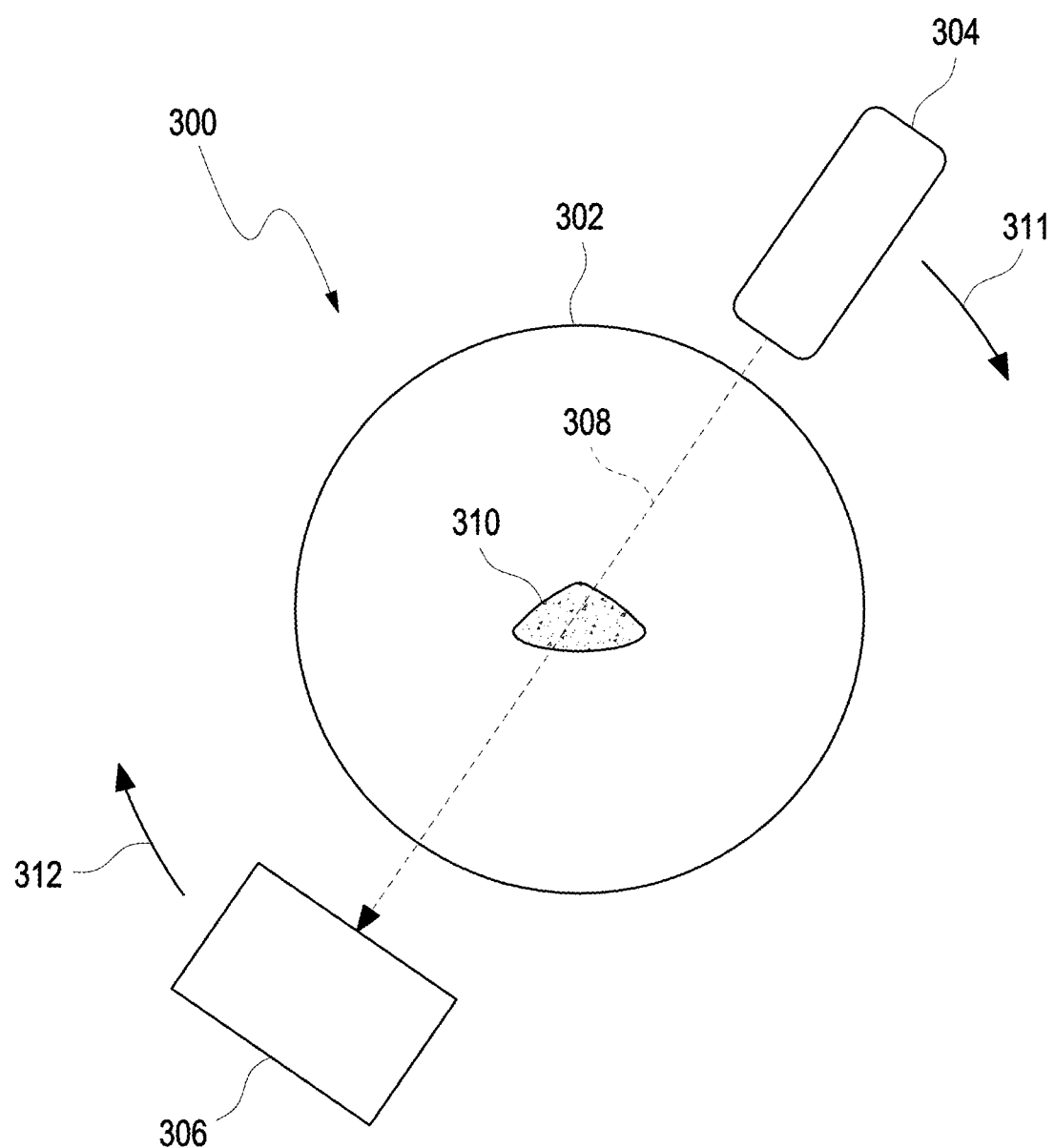

Similarly, FIG. 3 illustrates a top view of the C-arm scanner system shown in FIG. 2. Both the source 201, 304 and the detector 202, 306, which is preferably closed directly opposite to the source in one line through the object to be imaged 106, 203, 302, 310. In order to acquire projections at different projection angles for reconstructing 3D images the source 201, 304 and the detector 202, 306 are rotated around the patient 203, 302, 310. In FIGS. 2 and 3, the rotation direction is indicated by reference numerals 204, 311, 312. In fact, the general CT acquisition process includes the source 201, 304, and the detector 202, 306 rotating around the patient 203, 302, 310 while measuring line integrals along the X-ray direction 308.

The algorithm performing the method according to the invention is implemented on the HPC 103. During the course of the intervention, the HCP 103 calculates the updated image in real time. Here, standard CT density values and imaging features that are different from the standard CT values such as dual-energy index or difference images between actual projections and forward projected data sets are used to track instruments and to constrain the compressed sensing criterion. The updated image is then provided to the interventionist by displaying the updated image on the display array 102. For display standard graphic volume display techniques, such as volume-rendering, surface-rendering or digitally reconstructed radiographs (DDR) are calculated from the volumetric dataset. The DDR are for example reconstructed from various angles which can depend on the radiologists selection or automatically depending on intrinsic imaging features so that the intervention guidance is optimized (e.g. perpendicular to the main movement direction of the catheter). Furthermore, angiographic features are incorporated into the DDR to provide a 3D road-mapping feature. All acquired projection images as well as all acquired temporal updates are stored in the HPC for later use, e.g. for a later reconstruction of bleedings and other modifications in soft tissue.

Additionally, the CT-scanner 101 can employ multiple X-ray sources as well as detectors up to arrays of X-ray sources combined with arrays of X-ray detectors. In such an embodiment different X-ray energies can be used and the instrument can comprise material that allows detection in dual-energy mode. Thus, characteristic absorption features of the instruments with respect to multiple radiation energy can provide further information on the instrument and its movement. This allows to track instruments using other means than standard CT absorption measurements and the detection of instruments is more robust.

FIG. 4.1 illustrates a flowchart 400 of the general CT workflow for 4D-CATH as proposed according to the present invention. In a first optional step, a number of projections fulfilling the Shannon-Nyquist criterion, i.e. a high number of projections is acquired at different projection angles. From these projections a tomographic reconstruction of a high quality prior image is performed. Herein the prior image serves as the first image of the object to be imaged. Furthermore, the instrument used during medical intervention on the object to be imaged is not present on the prior image. Therefore, the prior image comprises a volumetric image of the object to be imaged with high resolution prior to the intervention. In other embodiments, such a first image may be provided from a database, a different imaging technique or a more coarsely sampled set of projections.

After acquisition and tomographic reconstruction of the first image, the instrument to be guided during the medical intervention on the object to be imaged is placed. Thus, in step 402 an instrument, such as a catheter, may be placed for further medical intervention, e.g. on the heart. After the placement of the instrument and on its way through the object to be imaged low dose update data is continuously acquired in step 403 for guiding the instrument during the intervention. Furthermore, the low dose update data from step 403 is continuously reconstructed using the imaging method according to the present invention.

Thus after a normal dose scan, all following scans can be performed as under sampled scans with a lower dose, which can be performed continuously. In practical interventional radiology, this results in an undersampling factor of the order of 10 to 30 resulting in 8 to 35 frames per reconstruction. These are reconstructed 404 providing images that represent temporal updates comprising changes in the examined volume. Update images are reconstructed using an iterative algorithm to incorporate the prior information as well as the actual temporal changes in the iterative steps. During the intervention the interventionist is continuously provided with updated images on-the-fly. Here the image diagnostically relevant for the physician is the sum of the prior image and the temporal change which is called the updated image.

FIG. 4.2 shows a flowchart 500 of the CT image acquisition and reconstruction. For the intervention in step 501 a high resolution, highly sampled CT scan is acquired as prior image. This image includes volumetric data representing the object to be imaged. During the intervention the prior image is used as a first image incorporated in the iterative construction algorithm during the intervention.

While performing the intervention by placing the instrument and moving it within the object to be imaged update information is continuously acquired in step 502. The update information comprises undersampled sets of projections, which allow for a low-dose rate. In order to reliably reconstruct images for the physician performing the intervention, this update information is incorporated with the prior image in step 503. Hence, the update information including the change of information corresponding to the moving instrument can be reconstructed in step 504 providing updated image data. Thus, the static part of the image is provided by the prior image, while the update information comprising a set of undersampled projections provides the temporal changes, which correspond to the moving instrument. This way a Prior Image Dynamic Computed Tomography (PRID-ICT) may be realized allowing for real-time interventional guidance. Optionally, the projections measured during the intervention in step 502 may after reconstruction in step 504 be used to update the prior image. By the calculation of a new prior image any temporal changes occurring during the intervention, such as movement of patient, can be incorporated over time into the prior image leading to a higher image quality.

Furthermore, the update information comprising undersampled sets of projections may be collected in step 506 during the course of the intervention. After or during the intervention, but with a larger time delay than for 504, the collected data sets from step 506 may be reconstructed in step 508 to visualize changes on a slower time scale than instrument movements, such as bleedings. For this different reconstruction algorithms can be used, including algorithms with further sparsifying functions.

FIG. 5 shows an overview of the proposed reconstruction algorithm in relation to the amount of data that is acquired from the actual present (514). The continuous acquisition of low-dose tomographic data during the intervention 510 leads to a constantly increasing amount of projections from a time 514 (represents present) to a time 515 in the past. The longer ago from the present the higher the amount of low-dose tomographic data 512 that has been acquired. Thus at point 516.1, a short time after the present, the amount of tomographic data 512 only comprises a few projections. Longer time ago 516 the amount of low-dose tomographic data 512 increases by increasing the number of projections measured. At a point 516.2 in time, the number of projections measured during the intervention, i.e. the amount of low-dose tomographic data 512, is increased.

At the earlier point in time 516.1, the measured data is used 518.2 to reconstruct and display temporal changes, such as movement of guide wires or catheters 526. The reconstruction in step 521 can, e.g. be performed by using compressed sensing, where the sparsifying is done through a difference with e.g. the first image.

At a later point in time 516.2, the full amount of low-dose tomographic data 512 corresponding to the projections measured until then can be used 518.1 to visualize the anatomy, bleedings, bones, organs or other static data 524. Here, the reconstruction 520 can be performed using compressed sensing including further sparsifying functions such as gradient functions. The sparsifying functions can thereby be selected so that larger, more areal changes to the dataset will prevail, while shorter, more punctual changes will not be reconstructed. Furthermore, the data reconstructed after time period 516.2 may be fed back 528 into the reconstruction algorithm during intervention as a first image. Apart from the exemplary embodiments shown in FIG. 5, many more time points (such as 516.1 and 516.2) with different reconstruction algorithms, different sparsifying algorithms and different contributions to the displayed images exist and the person skilled in the art may adapt the explicit execution to the specific needs of the medical intervention.

Figure 6:
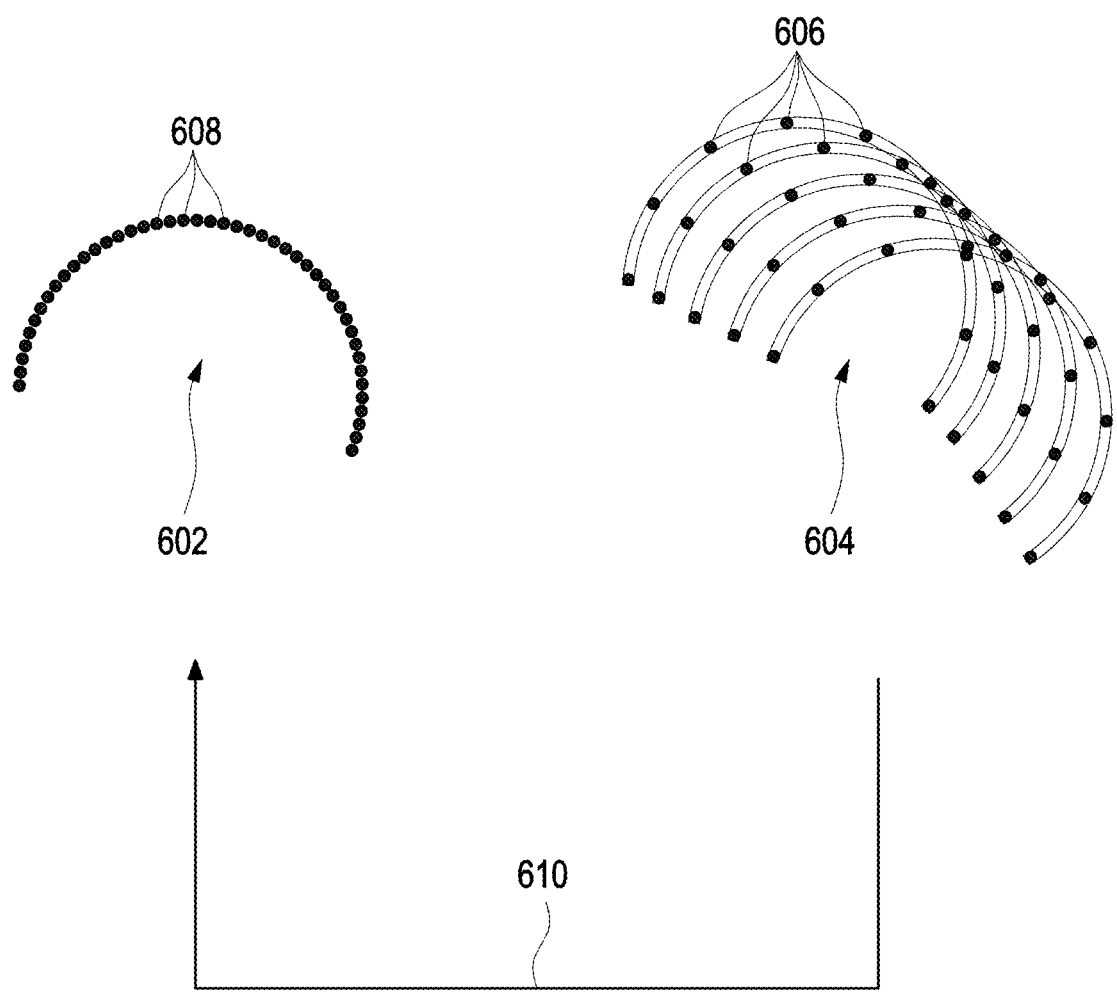

FIG. 6 illustrates how undersampled sets of projections 604 collected during the intervention may be defragmented for creating a fully sampled set of projections 602 which again may be used as updated first image (sliding prior). For a sliding prior, individual projections of the undersampled sets of projections 606 are culminated in accordance with their solid angle 608. The projections of the update scans 606 are acquired at angular positions that are different from earlier projection positions so that after several rotations a new-fully sampled dataset is produced which can be used as a sliding prior. In the sliding prior, the changes (e.g. catheters, guidewires, etc.) are removed via standard image processing algorithms. Such algorithms can be similar to those being used in metal artifact reduction, where the reconstruction including high contrast signals is followed by the segmentation of high contrast signals and the elimination of these high contrast structures in projection data via forward projection of segmented high contrast data. The new reconstruction can then be performed without high contrast data. Alternatively or additionally, algorithms that track instruments can be used. There e.g. connected pixels in the data set can be identified, a comparison with a data base of possible instruments can be performed or the PRIDICT (Prior Image Dynamic Computed Tomography) algorithm may even be modified so that significant pixels from the update will be memorized and removed. Other possibilities or additions may include dual-energy information e.g. through instruments, that provide a characteristic dual-energy signature.

Figure 7:
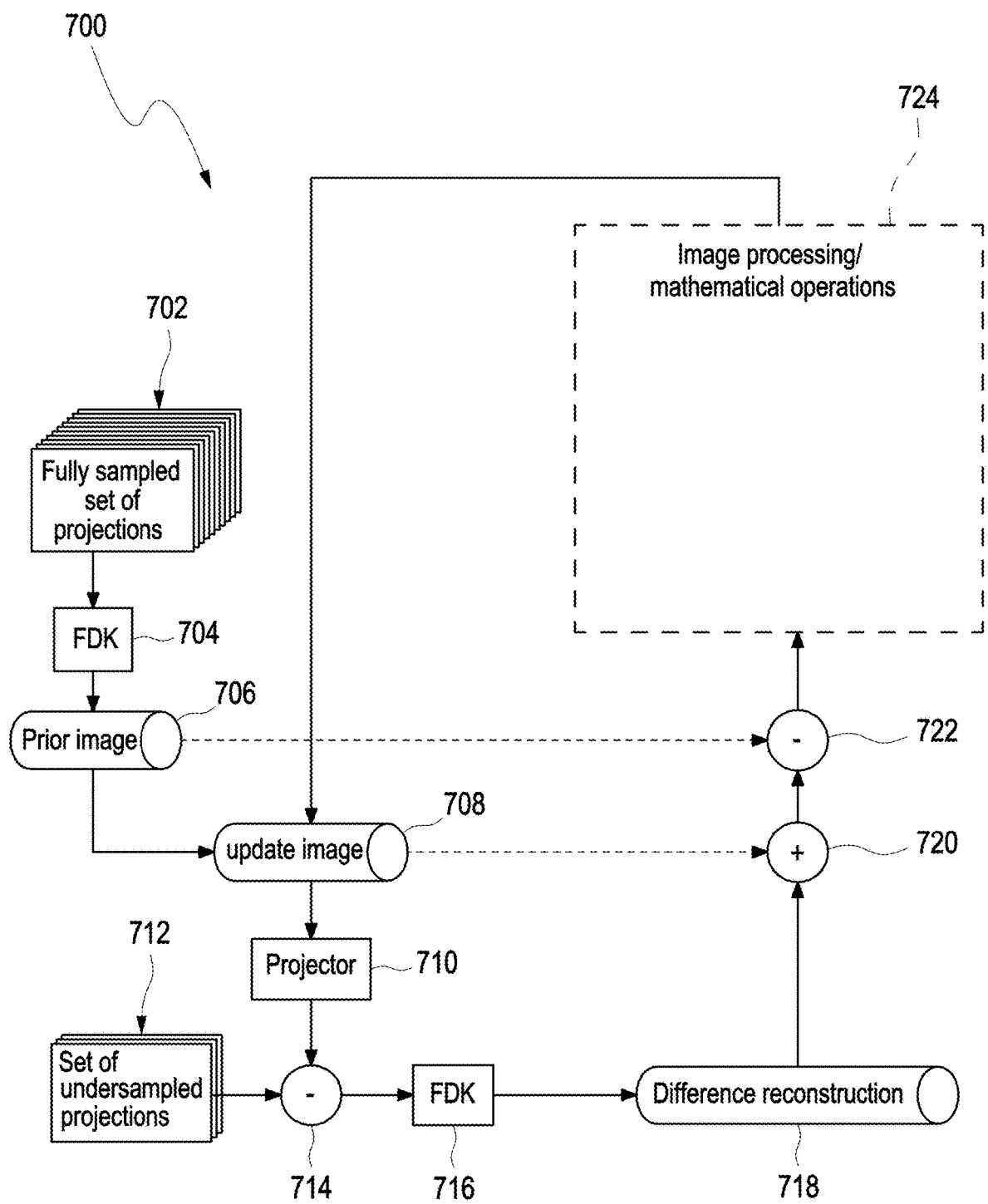

FIG. 7 shows a flowchart 700 illustrating the general structure of the PRIDICT reconstruction algorithm that can be used for 4D-CATH. The proposed algorithm PRIDICT is a reconstruction technique specialized to interventional 3D and 4D applications. It incorporates the information of a former scan (prior scan) to the reconstruction process and can reduce the number of relevant measurements for temporal updates far under the Shannon-Nyquist sampling using the compressed sensing framework.

The interventional procedure starts with the acquisition of a fully sampled, normal dose scan 702 that can be used a prior image for the PRIDICT reconstruction algorithm as well as a first overview CT scan for the physician. This fully sampled scan can be reconstructed in step 704 through a standard CT reconstruction algorithm such as the FDK (Feldmann Davis Kress, as for example explained in Feldkamp L A, Davis L C, Kress J W. Practical cone-beam algorithm. J. Opt. Soc. Am. 1984; 1(6):612-619) to provide a prior image 706. The prior image 706 forms the basis image 708 for the iterative PRIDICT reconstruction algorithm.

During the intervention undersampled sets of projections 712 are measured. These provide the update information including static as well as dynamic components of the object to be imaged. In a first step of the algorithm, the image 708, which in the first iteration is equal to the prior image and includes volumetric data, is projected in accordance with the projection angles measured in the undersampled set of projections 712. The projected data 710 from the image 708 is then subtracted individually from the update projections of the undersampled set of projections 712 in operation 714.

The subtraction in operation 714 leads to difference images 716, which represent the difference between the undersampled set of projections and the projected prior image. These difference images 716 are reconstructed through a standard reconstruction routine in CT such as FDK to provide a reconstructed and fully volumetric difference image 718. In operation 720, the image 708, which in the first run corresponds to the prior image 706, is added to the volumetric difference image 718. In operation 722, image 706, which is the prior image and stays the prior image for every iteration, is subtracted. In the following steps 724, various image processing and mathematical operations, such as optimization routines, may be used to modify the image. This image is fed back into the iterative loop and serves as the base image 708 for the next iteration of the reconstruction algorithm.

Figure 8:
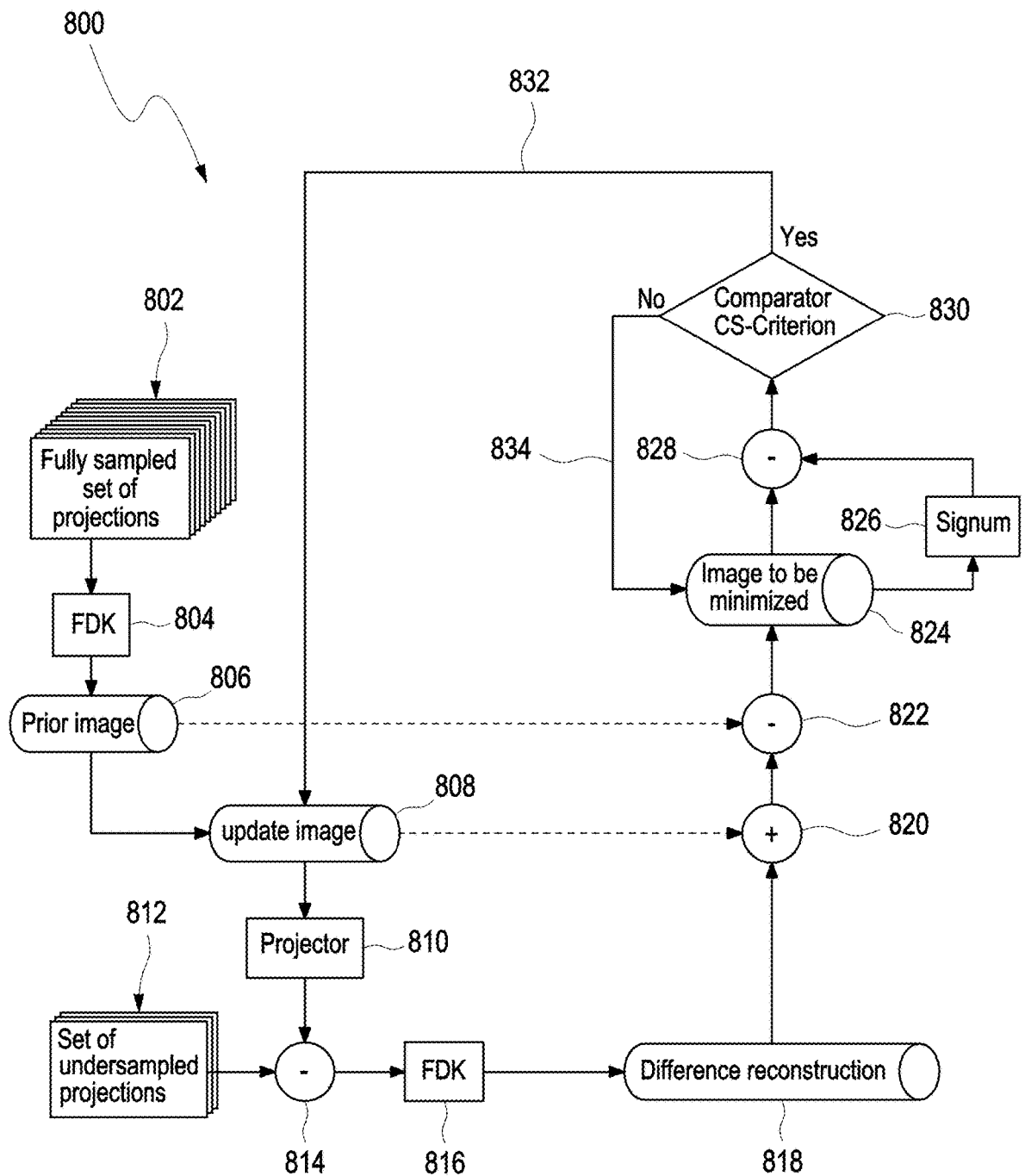

In FIG. 8, the PRIDICT algorithm 800 is illustrated including a minimization loop in place of the mathematical operations performed in step 724 of FIG. 7. Equivalently to FIG. 7 a fully sampled set of projections 802 is measured, reconstructed via the FDK algorithm 804 to a volumetric data set 806, which is fed into the image 808 forming the basis of the PRIDICT algorithm. Then difference images 818 are reconstructed in 816 from the subtraction of the projections of the undersampled set of projections 812 and the projections projected from the image 808 in step 814. Then image 808 is added in step 820 following a subtraction of prior image 806 in step 822. Thus, the resulting image 824 excludes any static components and highlights the change happened in the intervention during the measurement of the undersampled set of projections 812.

In place of step 724 in FIG. 7, the embodiment of FIG. 8 basically includes a minimization routing minimizing the number of significant pixels. The temporal updates are calculated as the FDK (Feldkamp-Davis-Kress) reconstruction of the difference of the actual measured projections and the calculated forward projections of the prior image. These FDK reconstructions contain only information of the current changes in the image but include a large number of streaking artifacts. To reduce these streaking artifacts, the total number of significant pixels (represented by the L0 norm) has to be minimized. Mathematically, the minimization of the L0 norm is difficult, so the L1 norm can be minimized alternatively, e.g. by using the method of the steepest gradient, other convex optimization techniques can also be used. Without constraints, the global minimum would be a zero matrix; however in practice this would imply no changes in the volume so that the prior image and the current image are identically. To eliminate the streaking artifacts without clearing the whole update, the minimization step has to be adjusted to the FDK reconstruction step, so that raw data congruence is aimed. This is presented in the next paragraph.

Without constraints, the global minimum of the L1 norm would be a zero matrix, but in fact this would eliminate any information in the update image. The link between the minimum number of independent probes and the number of significant pixels in the image: m≈S ln(N) where N×N is the size of the reconstruction matrix, S is the number of significant pixels and m is the number of independent probes. Using this context, the maximum number of significant pixels in an image can be calculated for every given acquisition scenario. We call this context the CSC (compressed sensing criterion). The minimization process is continued as long as the CSC is not fulfilled. As soon as the L0 norm is smaller than the calculated maximum number of significant pixels, the CSC is reached, the minimization stops and the next iteration is performed. The L1 norm has not to be minimized directly, even optimizations minimizing L1 casually might be useful.

As described, L1 is minimized because of the mathematically difficulties minimizing L0. The actual aim is to minimize L0, so in an embodiment of the algorithm, other optimizations minimizing L0 casually or directly may be used, even if they do not minimize L1.

Within the minimization loop after operation 822, the signum of the image 824 including only the temporal changes is calculated in 826 and subtracted from the image 824 in operation 828. From there it can be checked whether the compressed sensing criterion 830 is fulfilled. If it is fulfilled, the image is fed back into 808 replacing this image and image 808 can be displayed to the operator. If the compressed sensing criterion in 830 is not fulfilled, the image will be fed back into the compressed sensing minimization loop to 824. In contrast to the reconstruction algorithm shown in FIG. 8, FIG. 9 includes a further sparsifying transform 936 performed before the minimization of the number of significant pixels. As sparsifying transform 936 gradient operations, wavelet transfomations, curvelet transformations, contourlet transformations or a combination therof can be used. This transform is then applied after reconstructing the difference 918 and before the minimization loop is entered in 924.

In step 936 it is also possible to use a combination of different transforms and/or tunable transformations, which can be used in different configurations during one reconstruction, to correctly reconstruct different structures point-like or curve-like structures. Furthermore, the weight of different sparsifying transforms can be varied e.g. according to the sparseness of the transformed image.

The realization of such a tunable PRIDICT reconstruction algorithm 1000 is shown in FIG. 10.1. The algorithm shown in FIG. 10.1 corresponds to the algorithm shown in FIGS. 7 to 9. The embodiment of FIG. 10, however, incorporates the image processing and mathematical operations 1024 including the minimization loop 1028 for finding an optimal difference image and a pre-applied sparsifying function 1026. Here, the sparsifying function as well as the minimization loop 1028 may be influenced by the actual difference 1030 given in the static prior set of projection 1002 and the undersampled set of projections 1012 including the temporal changes. So certain parameters of the mathematical functions, i.e. the sparsifying function and the minimization, may be modified in accordance with a comparison 1030 done between the prior set of projections 1002 and the undersampled set of projections 1012. Thus, the reconstruction algorithm PRIDICT 1000 can be tuned and adapt to different situations depending on the temporal changes. This is particularly advantageous when reconstructing temporal changes from guide wires, catheters, tubes and the like or temporal changes which move much slower such as bleedings.

FIG. 10.2 shows further possibilities for influencing the reconstruction of updated images. The flowchart 1040 comprises in step 1042 the acquisition of undersampled imaging data during the intervention. From this data and the previously acquired prior image or an updated prior image the amount of difference and/or movement in the examined volume is calculated in step 1044. Then the calculated amount of difference and/or movement can be used to influence scan parameters and/or reconstruction parameters, such as the number of projections included into the undersampled set of projections, in step 1046. Optionally, such influences can also be triggered from the outside such as an operator 1052. Furthermore, these influences are used to vary the reconstruction algorithm 1048, such as reconstruction matrix size, time resolution, sparsifying function and so on. Lastly, a marker for the degree of completeness of the imaging data may be provided in operation 1050.

Figure 9:
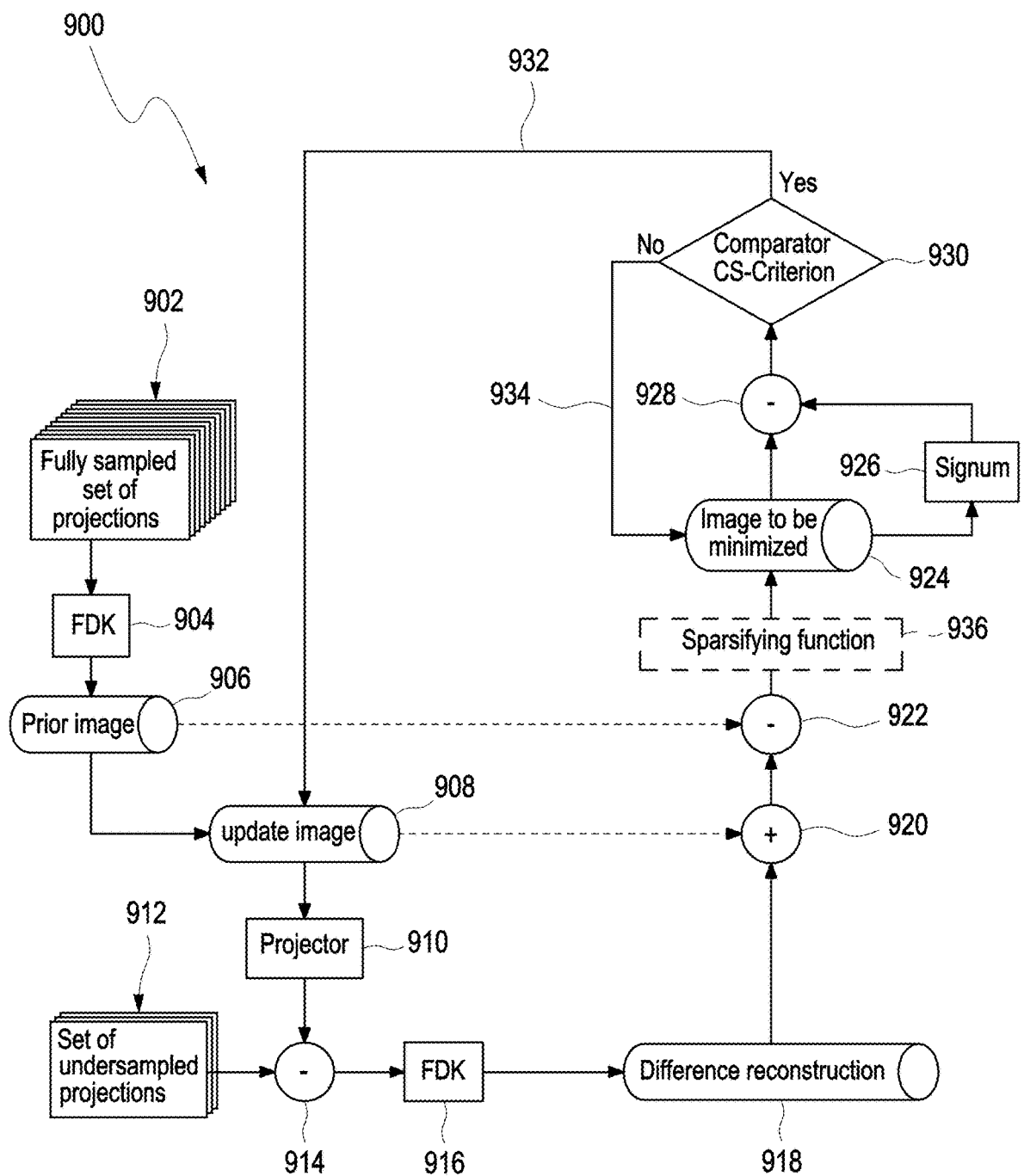
Figure 11:
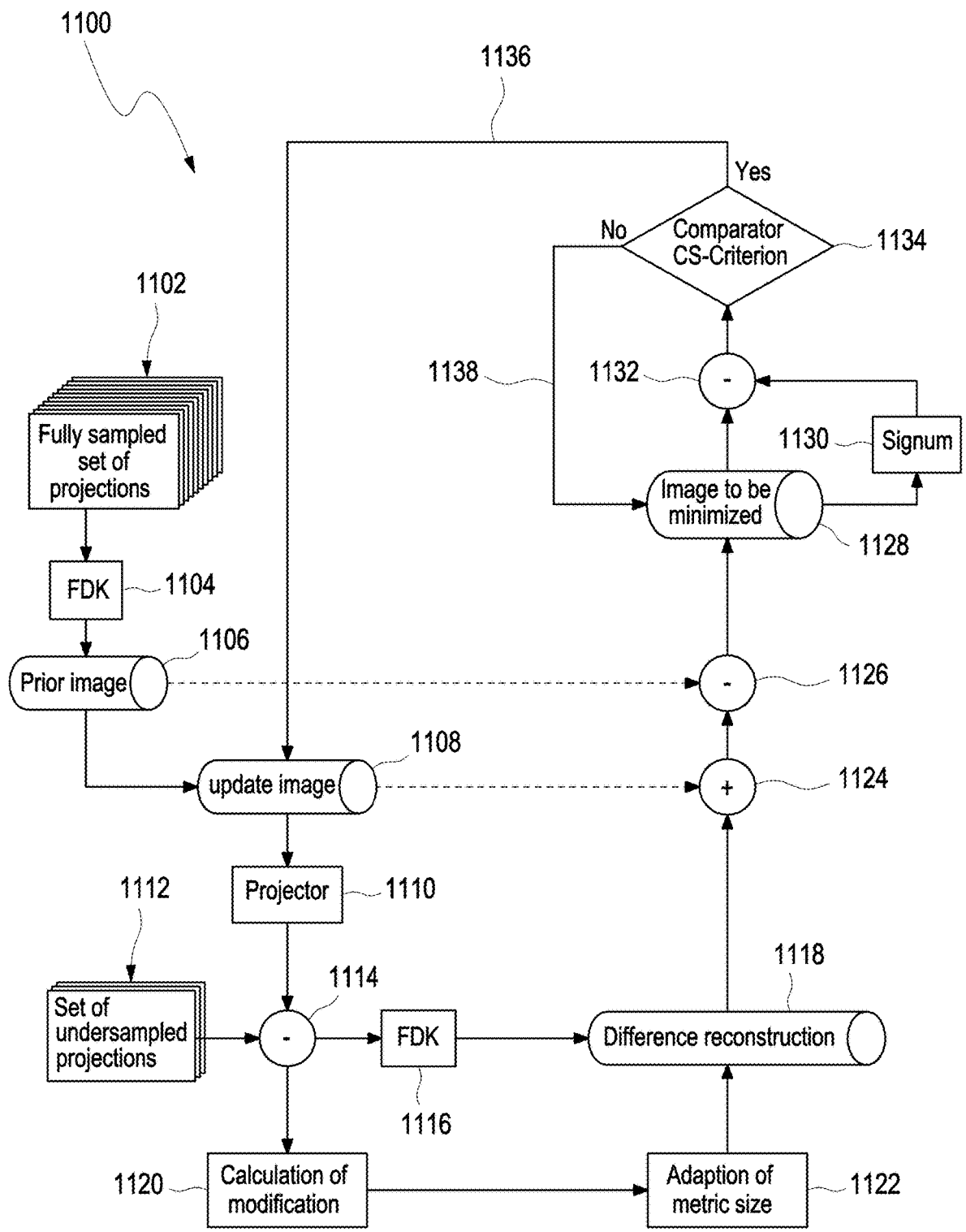

In order to provide a parameter of completeness, FIG. 11 shows another realization of the PRIDICT reconstruction algorithm 1100, which broadly corresponds to the reconstruction algorithm PRIDICT shown in FIGS. 7 to 9. Here the subtraction 1114 is not only used to calculate the difference image 1116 but also to calculate the total modification 1120 in the image. From there, the matrix size can be set 1122 which can be fed back to the difference reconstruction image 1118. This results in optimized reconstruction minimization of the significant number of pixels. Thus, if there is a large change the modifications are large and the matrix size may be smaller. On the other hand, if the changes between the prior image data and the undersampled set of projections are small, the modifications are small and the matrix size may be set to a larger value in order to reconstruct the difference properly.

FIG. 12 illustrates the effect of the proposed PRIDICT reconstruction algorithm on a head. A pig head was scanned prior to the intervention, the result of which is shown in FIG.

12.1. After the insertion of a guide wire into an arteria a temporal update was provided. Here, FIG. 12.2 shows the reconstruction of the undersampled set of projections using a standard FDK algorithm. In comparison to FIG. 12.1 showing the result reconstructed by a standard FDK algorithm of the fully sampled prior image, FIG. 12.2 includes streaks and artifacts. In FIG. 12.3, the result including the guide wire is shown reconstructed through the PRIDICT reconstruction that uses a fully sampled prior image and an undersampled set of projections. As can be seen, the result of FIG. 12.3 is artifact-free and the magnified inset shows the wire labeled through the smaller arrow and the vessel through the larger arrow.

Figure 13:
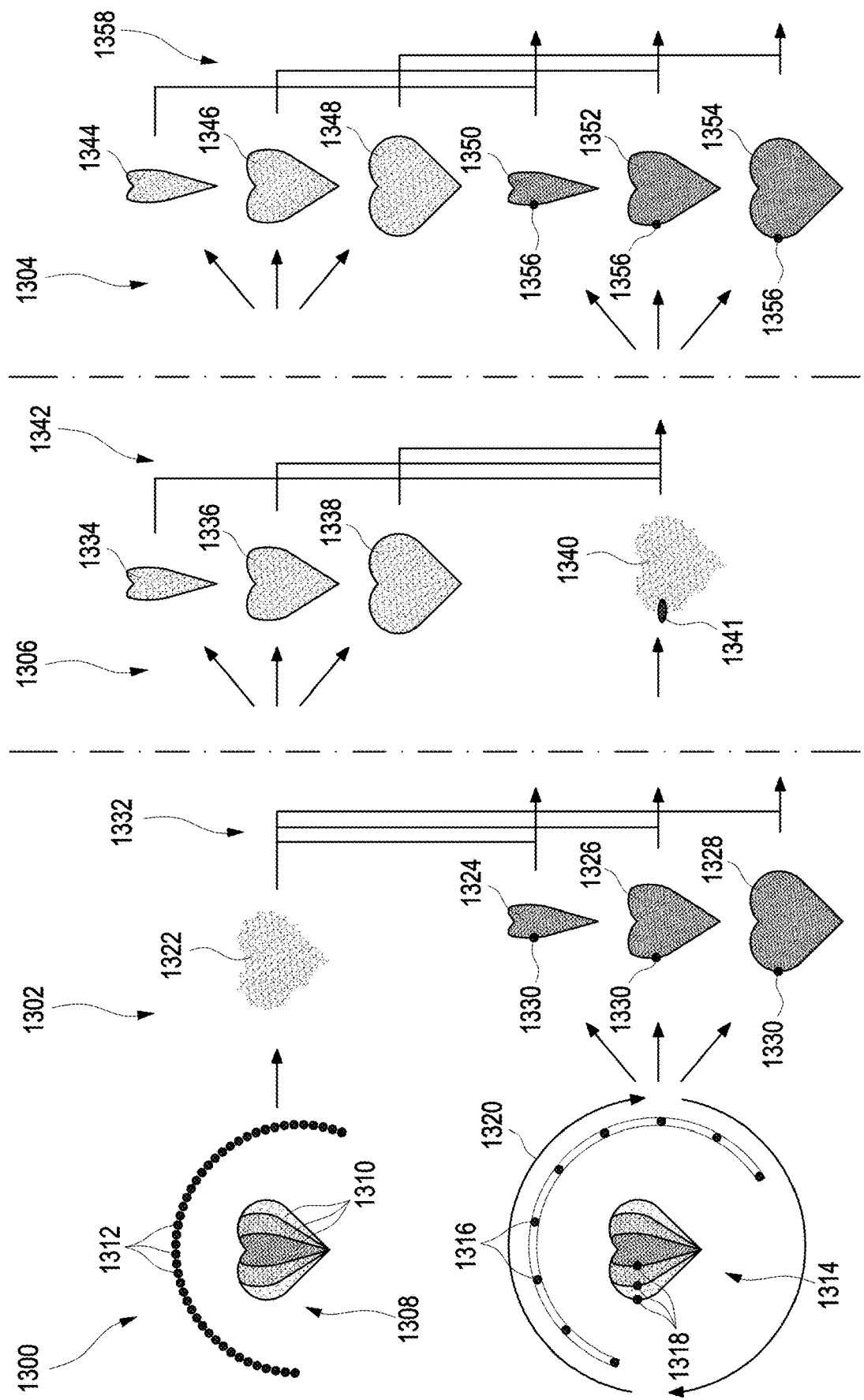

FIG. 13 illustrates different embodiments 1302, 1306, 1304 for motion compensated reconstruction in connection with the proposed PRIDICT reconstruction algorithm. In the first column 1300 of FIG. 13, a prior image 1308 reconstructed from a fully sampled set of projections 1312 includes different phases 1310 of the cardiac motion. As a consequence of the cardiac motion, its appearance changes from projection to projection. Therefore, the prior image 1308 results in a smeared image of the heart 1322, which is smeared by the heart motion during the measurement. The bottom part of column 1300 illustrates the corresponding undersampled set of projections where different projections represent different cardiac phases 1318 as well. Here again the heart 1318 periodically changes appearance for the different cardiac phases 1318 from projection to projection 1316.

Column 1302 illustrates one implementation for motion-gated reconstruction. Under the assumption that the heart appearance is the same for a single cardiac phase over the entire scan time, a gating is performed to assort the acquisition into the heart cycle which itself is divided into phase bins with sufficiently small widths. Thus, the displacement of the heart is taken into account for e.g. each projection measured in the undersampled set of projections. In the example illustrated in column 1302, bottom part, the undersampled set of projections 1316 is binned into three different phases of the heart beat cycle 1324, 1326, 1327. These phases may for instance be monitored throughout the intervention, e.g. through electrocardiography, and the binning is carried out in accordance with the monitored reference signal. Incorporating the prior image 1322 using the PRIDICT algorithm to reconstruct the heart in each individual phase 1324, 1326, 1327 results in update images which show the instrument 1313 in the equivalent place for each cardiac phase 1324, 1326, 1327. This way, the smearing due to the heart motion can be compensated for and the temporal change due to the instrument 1313 can be reconstructed according to the cardiac phases 1324, 1326, 1327. Thus, the interventionist can at each point during the intervention assess where within the heart the instrument is situated. Owing to the reduced smearing resulting from the cardiac motion a more accurate position of the instrument 1313 within the heart can be displayed to the operator. The advantage of such an algorithm is that there is no gating signal necessary for the prior image.

In column 1306 another implementation of motion-compensated reconstruction via PRIDICT is illustrated. In this case the prior image 1308 is binned into the cardiac phases 1334, 1336, 1338 rather than the reconstructed update image 1340. Here no gating signal is necessary for the reconstruction of the heart phases and thus, slower scanner systems might be utilized.

Column 1304 shows another implementation of motion-gated reconstruction through PRIDICT. Here, rather than reconstructing the time frames with respect to cardiac and/or respiratory phases or the prior as shown in columns 1302, 1306, the prior as 1308 well as the time frames 1314 may be reconstructed with respect to the cardiac and/or respiratory phase using compressed sensing reconstruction. In this embodiment, gating is necessary for the prior as well as the update image and images can be reconstructed with less motion-related smearing.

Furthermore, the reconstruction scan can be incorporated with low dose update scans using motion-compensated reconstruction combined with compressed sensing and taking a 4D representation of the moving heart into consideration. The idea of motion-compensated 4D reconstruction may also be deeply integrated into the reconstruction algorithm. In order to do so, the cardiac and/or respiratory phases are registered or the transformation may be done through morphing or movement field. By using a transformation the image may be projected into either the moving space or a static space. In a static space the object to be imaged may be displayed in one phase only, which is particularly useful for the guidance of catheters. Furthermore, the requirements to the scanning speed are relaxed. With appropriate motion-compensating reconstruction algorithms (including movement vector fields) the data that is acquired at a certain heart phase can be used to reconstruct images at a different heart phase.

Figure 14:
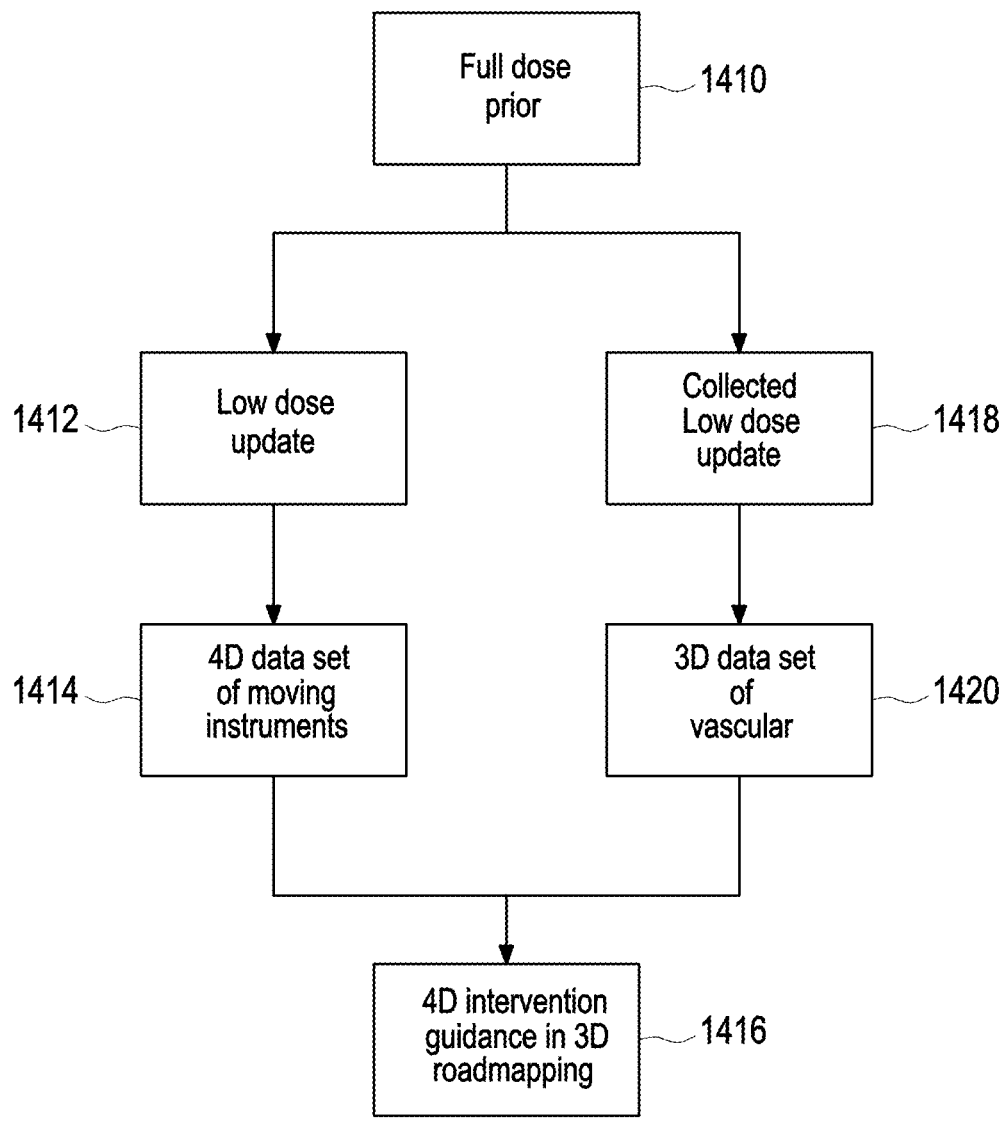

FIG. 14 shows an overview illustrating the capability of the PRIDICT reconstruction algorithm. Starting from a full dose prior image 1410 of the object to be imaged during intervention with a moving instrument low dose updates 1412 are acquired. From these low dose updates a 4D data set of the moving instrument 1414 may be reconstructed. Furthermore, the low dose updates 1418 may be used to reconstruct the 3D data set of a body part with intervascular contrast media 1420. Lastly, the 4D data set of the moving instrument 1414 and the 3D data set of the vascular structure 1420 can be merged to a 4D intervention guidance in 3D road-mapping 1416. Thus, the movement of the instrument during the intervention may be visualized after the intervention in the form of a roadmap illustrating the full course of the intervention.

In one embodiment of the invention the method for performing imaging during radiological interventions, comprises the steps of measuring more than one set of projections of an object to be imaged at different points in time, wherein the measurement is performed by an imaging apparatus and dynamic reconstruction of volumetric datasets from the more than one set of projections, wherein the reconstruction is performed by processing means. In a further embodiment of the invention, the more than one set of projections of the object to be imaged are measured in a repetitive or continuous scanning mode of the imaging apparatus. In a further embodiment of the invention, the processing means comprise a processor. In yet a further embodiment of the invention, the more than one set of projections of the object to be imaged comprise undersampled sets of projections. In a further embodiment of the invention, the undersampled sets of projections are measured at consecutive points in time during the radiological intervention. In a further embodiment of the invention, the more than one set of projections of the object to be imaged comprises at least one fully sampled set of projections, preferably measured before, during or after the radiological intervention. In a further embodiment of the invention, the reconstruction is performed by an iterative reconstruction method. In a further embodiment of the invention, the iterative reconstruction method is based on compressed sensing theory. In a further embodiment of the invention, the variations in an algorithm for the reconstruction are matrix size, interruption criterion, sparsifying functions. In a further embodiment of the invention, the interruption parameter of the iterative reconstruction method is depending on the amount of changes in the volumetric datasets reconstructed from the undersampled sets of projections, the amount of significant pixels and/or the used sparsifying function. In a further embodiment of the invention, the more than one set of projections of the object to be imaged comprise at least one fully sampled set of projections and undersampled sets of projections measured at consecutive points in time during the radiological intervention, wherein the reconstruction is configured to combine the at least one fully sampled set of projections with undersampled sets of projections. In a further embodiment of the invention, imaging parameters of the imaging apparatus depend on the amount of movement and information changes in an examination volume. In a further embodiment of the invention, the dependency on the amount of movement and information changes in the examination volume is influenced by the interventionalist. In a further embodiment of the invention, the step of the reconstruction is influenced by the amount of changes in the object to be imaged. In a further embodiment of the invention, a user is provided with some means to influencing the ratio how changes in the examined volume influence the data acquisition, reconstruction parameters or data display.

In another aspect of the invention, the method described above is for use during radiologically guided interventions on the cardiovascular system. In a further aspect of the invention, the method described above is for use in the implantation of cardiac pacemakers. In a further aspect of the invention, the method described above is for use during radiologically guided interventions on tubular organ structures, preferably lungs or kidneys. In a further embodiment of the invention, for use in positioning of stents in vessels or bronchi. In a further aspect of the invention, the method described above is for use during bronchoscopy interventions. In a further aspect of the invention, the method described above is for use during catheter interventions. In a further aspect of the invention, the method described above is for use during radiologically guided interventions on the brain.

In one embodiment of the invention a system for carrying out the method as described above, contains an imaging apparatus in communication with processing means, wherein the imaging apparatus is a tomographic system, such as a magnetic resonance imaging (Mill) scanner or a computed tomography (CT) scanner. In another embodiment of the invention the computed tomography scanner comprises at least one X-ray source and at least one detector, wherein the X-ray sources differ in terms of the X-ray spectra or the detectors providing means of energy differentiation.

LIST OF REFERENCE NUMERALS

100 Scan system
101 CT scanner
102 Array of displays
103 HPC
104 Operator control
105 Operator
106 Patient
201 Source
202 Detector
203 Object to be imaged
204 Rotation direction
300 Imaging system
302 Object to imaged
304 Source
306 Detector
308 X-ray
310 Structure within the object to be imaged
311, 312 Rotation direction
400 Flow chart 4D-CATH during the intervention
402 Catheter placement
403 Acquisition of update data
404 Reconstruction of acquired data
500 Flowchart of 4D-CATH
501 Acquisition of high resolution CT scan
502 Performing intervention and acquiring update information
503 Incorporation of prior image
504 Reconstruction of image data
506 Collection of data
508 Reconstruction of soft tissue image; new prior
510 Continuous acquisition of low dose tomographic data during intervention
514 Situation X
512 Amount of tomographic data available
515 Situation X t
516 Time axis
516.1, 516.2 Points in time
518.1, 518.2 Processing of data available
520 Reconstruction with further sparsifying function and/or prior image sparsifying
521 Reconstruction without further sparsifying function
524 Display of anatomy
526 Display of guide wires
528 Feedback for prior image
602 Prior image
604 Update scans
606 Projection at a solid angle for update scans
608 Projection at a solid angle for prior image
610 Incorporation of update scans in prior
700 PRIDICT reconstruction algorithm
702 Fully sampled set of projections
704 FDK
706 Prior image
708 Update image
710 Projector
712 Set of undersampled projections
714 Subtraction operation
716 FDK
718 Difference reconstruction
720 Summing operation
722 Subtraction operation
724 Image processing, mathematical operations
800 PRIDICT reconstruction algorithm including minimization
802 Fully sampled set of projections
804 FDK
806 Prior image
808 Update image
810 Projector
812 Set of undersampled projections
814 Subtraction operation
816 FDK
818 Difference reconstruction
820 Summing operation
822 Subtraction operation
824 Image to be minimized
826 Signum of image to be minimized 828 Subtraction operation
830 Comparator CS criterion
832 Image reconstruction loop
834 Minimization loop
900 PRIDICT reconstruction algorithm including sparsifying function
902 Fully sampled set of projections
904 FDK
906 Prior image
908 Update image
910 Projector
912 Set of undersampled projections
914 Subtraction operation
916 FDK
918 Difference reconstruction
920 Summing operation
922 Subtraction operation
924 Image to be minimized
926 Signum
928 Subtraction operation
930 Comparator CS criterion
932 Image reconstruction loop
934 Minimization loop
936 Further sparsifying function
1000 PRIDICT reconstruction algorithm including influence of reconstruction parameters
1002 Fully sampled set of projections
1004 FDK
1006 Prior image
1008 Update image
1010 Projector
1012 Set of undersampled projections
1014 Subtraction operation
1016 FDK
1018 Difference reconstruction
1020 Summing operation
1022 Subtraction operation
1024 Image processing, mathematical operation
1026 Sparsifying function
1028 Minimization
1030 Comparison of prior and update scans
1032, 1034 Influence on reconstruction algorithm
1040 Flow chart for adapting PRIDICT
1042 Continuous acquisition of undersampled data
1044 Calculation of amount of difference/movement
1048 Variation in reconstruction algorithm
1050 Providing a marker for the degree of completeness
1052 Input from radiologist
1046 Influencing scan parameters reconstruction parameters
1100 PRIDICT reconstruction algorithm including influence
1102 Fully sampled set of projections
1104 FDK
1106 Prior image
1108 Update image
1110 Projector
1112 Set of undersampled projections
1114 Subtraction operation
1116 FDK
1118 Difference reconstruction
1120 Calculation of modification
1122 Adaption of metric size
1124 Summing operation
1126 Subtraction operation
1128 Image to be minimized
1130 Signum
1132 Subtraction operation
1134 Comparator CS criterion
1136 Image reconstruction loop
1138 Minimization loop
1200 Guide wire
1300 Prior image
1302 Time frame reconstruction of update
1304 Time frame reconstruction of prior and update
1306 Time frame reconstruction of prior
1308 Heart to be fully imaged
1310 Cardiac phases
1312 Projections of prior
1314 Heart to be imaged through undersampled set
1316 Projection of undersampled set
1318 Cardiac phases
1320 Rotation
1322 Reconstructed prior
1324 Reconstructed update in cardiac phase 1
1326 Reconstructed update in cardiac phase 2
1328 Reconstructed update in cardiac phase 3
1330 Instrument
1332 Prior incorporated into each reconstruction of cardiac phases
1334 Reconstructed prior in cardiac phase 1
1336 Reconstructed prior in cardiac phase 2
1338 Reconstructed prior in cardiac phase 3
1340 Reconstructed update
1341 Instrument
1342 Prior for cardiac phases incorporated into reconstruction
1344 Reconstructed prior in cardiac phase 1
1346 Reconstructed prior in cardiac phase 2
1348 Reconstructed prior in cardiac phase 3
1350 Reconstructed update in cardiac phase 1
1352 Reconstructed update in cardiac phase 1
1354 Reconstructed update in cardiac phase 1
1356 Instrument
1358 Prior for cardiac phases incorporated into reconstruction of update for cardiac phases
1410 Full dose prior
1412 Low dose update
1414 4D data set of moving instruments
1416 4D intervention guidance in 3D road map
1418 Collected Low dose updates
1420 3D data set of vascular

The invention claimed is:

1. An imaging method, the method comprising:
providing a final image of said object by: providing updated images on the fly by real time imaging during an intervention to an operator by repeatedly
measuring an undersampled set of projections of said object, and
reconstructing said updated images to provide the final image using compressed sensing based on changes between an update of a first image and said undersampled set of projections;
wherein the compressed sensing reconstruction includes a first sparsifying function comprising an iterative minimization of a number of significant pixels and at least one further sparsifying function,
wherein the at least one further sparsifying function included in the reconstruction depends on an amount of data that has been acquired, and
wherein a number of projections in the undersampled set of projections and a dose rate per projection are adapted according to an amount of changes between successive measurements of the undersampled set of projections.

2. The method according to claim 1, wherein said imaging method is based on ionizing radiation and the undersampled set of projections is measured with a radiation dose.

3. The method according to claim 1, wherein said final image and said update of said first image comprise volumetric images of the object.

4. The method according to claim 1, wherein said first image is acquired prior to the intervention or is provided from a database.

5. The method according to claim 1, wherein said final image includes said first image and at least parts of one or more updated images reconstructed in previous runs during the intervention.

6. The method according to claim 1, wherein said undersampled sets of projections are measured on-the-fly and are stored for a delayed reconstruction of soft tissue contrast.

7. The method according to claim 1, wherein the updated images are reconstructed with no further sparsifying function beyond the at least one sparsifying function and wherein reconstruction of data stored from previous measurements includes the at least one sparsifying function.

8. The method according to claim 1, wherein the reconstruction is influenced by the amount of said changes between measurements.

9. The method according to claim 1, wherein the number of projections in the undersampled set of projections and the dose rate per projection are adapted according to an input provided by the operator.

10. The method according to claim 1, wherein the reconstruction of said updated image includes motion compensation.

11. The method according to claim 1, wherein periodic and/or non-periodic motion of the object is compensated for in the reconstruction of said updated images.

12. The method according to claim 1, wherein periodic motion compensation is performed through gating images into different phases of said periodic motion.

13. The method according to claim 1, wherein periodic motion compensation is performed through a transformation mapping said updated images and/or said first image into one phase of periodic motion.

14. The method according to claim 1, wherein said updated images are displayed on a screen allowing for different representation modes, which are chosen automatically or by said operator.

15. The according to claim 1, wherein the imaging method is a 4D method for radiological guiding.

16. The method according to claim 1, wherein the intervention is an intervention on the cardiovascular system.

17. The method according to claim 1, wherein the intervention is a catheter intervention or is a cardiac pacemaker implantation.

18. The method according to claim 1, wherein the intervention is an intervention on a tubular organ structure.

19. The method according to claim 1, wherein the intervention is an intervention on a kidney or lung.

20. The method according to claim 1, wherein the intervention is an intervention for positioning a stent in vessels or bronchi.

21. The method according to claim 1, wherein the intervention is a bronchoscopy.

22. The method according to claim 1, wherein the intervention is an intervention on the brain.

* * * * *

UNITED STATES PATENT AND TRADEMARK OFFICE
CERTIFICATE OF CORRECTION

PATENT NO. : 10,918,305 B2  
APPLICATION NO. : 13/991550  
DATED : February 16, 2021  
INVENTOR(S) : Jan Kuntz, Soenke Bartling and Marc Kachelriess Page 1 of 1

It is certified that error appears in the above-identified patent and that said Letters Patent is hereby corrected as shown below:

On the Title Page

Item (73), Delete:
"Assignee: Klinikum Mannheim Gmbh Universitatsklinikum Medizinische, Erlangen (DE); Fakultat Mannheim Der Universitat Heidelberg, Erlangen (DE)"

And Insert:
--Assignee: Deutsches Krebsforschungszentrum, Heidelberg (DE);
Klinikum Mannheim Gmbh Universitaetsklinikum Medizinische Fakultaet Mannheim der Universitaet Heidelberg, Mannheim (DE);
Friedrich-Alexander-Universitaet, Erlangen-Nürnberg (DE)--

Signed and Sealed this  
Twenty-eighth Day of December, 2021

Drew Hirshfeld  
*Performing the Functions and Duties of the*  
*Under Secretary of Commerce for Intellectual Property and*  
*Director of the United States Patent and Trademark Office*